(12) United States Patent
Percival et al.

(10) Patent No.: US 10,874,108 B2
(45) Date of Patent: Dec. 29, 2020

(54) ANTI-MICROBIAL COMPOSITIONS

(71) Applicant: 5D HEALTH PROTECTION GROUP LTD, Gwynedd (GB)

(72) Inventors: Steven Percival, Chester (GB); Rui Chen, Liverpool (GB); John Alan Hunt, Irby (GB)

(73) Assignee: 5D Health Protection Group Ltd., Gwynedd (GB)

( * ) Notice: Subject to any disclaimer, the term of this patent is extended or adjusted under 35 U.S.C. 154(b) by 0 days.

(21) Appl. No.: 16/098,629

(22) PCT Filed: May 4, 2017

(86) PCT No.: PCT/GB2017/051243
§ 371 (c)(1),
(2) Date: Nov. 2, 2018

(87) PCT Pub. No.: WO2017/191453
PCT Pub. Date: Nov. 9, 2017

(65) Prior Publication Data
US 2019/0133131 A1 May 9, 2019

(30) Foreign Application Priority Data

May 4, 2016 (GB) .................................. 1607814.9

(51) Int. Cl.
| | |
|---|---|
| A01N 55/02 | (2006.01) |
| A01N 59/16 | (2006.01) |
| C07C 229/16 | (2006.01) |
| A01N 37/44 | (2006.01) |
| A61L 15/44 | (2006.01) |
| C07F 1/08 | (2006.01) |
| C07F 1/10 | (2006.01) |
| C07F 3/06 | (2006.01) |

(52) U.S. Cl.
CPC ............. *A01N 55/02* (2013.01); *A01N 37/44* (2013.01); *A01N 59/16* (2013.01); *A61L 15/44* (2013.01); *C07C 229/16* (2013.01); *C07F 1/08* (2013.01); *C07F 1/10* (2013.01); *C07F 3/06* (2013.01); *A61L 2300/404* (2013.01)

(58) Field of Classification Search
None
See application file for complete search history.

(56) References Cited

U.S. PATENT DOCUMENTS

| | | | |
|---|---|---|---|
| 5,141,803 A | 8/1992 | Pregozen | |
| 5,362,754 A | 11/1994 | Raad et al. | |
| 5,602,180 A | 2/1997 | Bennett | |
| 5,688,516 A | 11/1997 | Raad et al. | |
| 5,998,488 A | 12/1999 | Shinohara et al. | |
| 6,056,939 A | 5/2000 | Desreux et al. | |
| 6,303,039 B1 | 10/2001 | Back et al. | |
| 6,509,319 B1 | 1/2003 | Raad et al. | |
| 6,638,431 B2 | 10/2003 | Back et al. | |
| 6,762,160 B2 | 7/2004 | Barbeau et al. | |
| 7,381,751 B2 | 6/2008 | Sarangapani | |
| 7,750,201 B2 | 7/2010 | Patel et al. | |
| 8,426,474 B2 | 4/2013 | Farng et al. | |
| 8,541,472 B2 | 9/2013 | Kite et al. | |
| 8,679,537 B2 | 3/2014 | Arthur | |
| 9,089,140 B2 | 7/2015 | McCullough et al. | |
| 9,155,720 B2 | 10/2015 | Kite et al. | |
| 9,339,492 B1 | 5/2016 | Farber et al. | |
| 9,603,966 B2 | 3/2017 | Rodeheaver et al. | |
| 9,821,063 B2 | 11/2017 | Herr et al. | |
| 9,980,497 B2 | 5/2018 | Gawande et al. | |
| 2002/0068079 A1* | 6/2002 | Laurie ................. | A61K 9/0019 424/422 |
| 2002/0162800 A1 | 11/2002 | Back et al. | |
| 2005/0048124 A1 | 3/2005 | Sarangapani | |
| 2006/0045899 A1 | 3/2006 | Sarangapani | |

(Continued)

FOREIGN PATENT DOCUMENTS

| | | |
|---|---|---|
| EP | 0494373 A1 | 7/1992 |
| EP | 1557180 A1 | 7/2005 |

(Continued)

OTHER PUBLICATIONS

PCT International Search Report for International Application No. PCT/GB2017/051243, dated Aug. 9, 2017, 13 pages.

(Continued)

*Primary Examiner* — Katherine Peebles
(74) *Attorney, Agent, or Firm* — Michael Best & Friedrich LLP

(57) ABSTRACT

A metal-EDTA compound/complex for combatting biofilms and/or treating wounds. The compound/complex comprises EDTA and from two to four metal ions. Of those two to four metal ions, at least two are different metal ions selected from Ag, Al, Au, Ba, Bi, Tl, Ce, Co, Cu, Fe, Ga, Ir, Mo, Rh, Ru, Ti, and Zn ions. The metal-EDTA compound/complex may exhibit any one or more of anti-microbial, anti-biofilm and anti-inflammatory activities in use and may increase the susceptibility of a biofilm and the microorganisms within said biofilm to attack by anti-microbial agents, helping to remove and sanitise the biofilm. A composition, wound dressing and medical device comprising the metal-EDTA complex are also provided. Uses of the metal-EDTA compound/complex as a medicament and/or to sanitise and/or substantially remove a biofilm from a substrate are also disclosed.

19 Claims, 3 Drawing Sheets

(56) References Cited

U.S. PATENT DOCUMENTS

| | | |
|---|---|---|
| 2008/0124368 A1 | 5/2008 | Sarangapani |
| 2010/0036334 A1 | 2/2010 | Heagle et al. |
| 2011/0189260 A1 | 8/2011 | Herr et al. |
| 2012/0077720 A1 | 3/2012 | Sloan |
| 2012/0213865 A1 | 8/2012 | McCullough et al. |
| 2013/0171224 A1 | 7/2013 | Percival et al. |
| 2016/0375078 A1 | 12/2016 | Wurts |
| 2017/0049749 A1 | 2/2017 | Ryan |
| 2017/0215417 A1 | 8/2017 | Bhushan et al. |
| 2017/0290789 A1 | 10/2017 | Dicosmo |
| 2018/0036410 A1 | 2/2018 | Herr et al. |

FOREIGN PATENT DOCUMENTS

| | | |
|---|---|---|
| EP | 1330440 B1 | 11/2007 |
| EP | 2082723 A1 | 7/2009 |
| EP | 1339416 B1 | 11/2012 |
| EP | 2306821 B1 | 10/2014 |
| WO | 01000221 A1 | 1/2001 |
| WO | 03047341 A2 | 6/2003 |
| WO | 2007068938 A2 | 6/2007 |
| WO | WO 2008/152444 A2 | 12/2008 |
| WO | WO 2009/155088 A1 | 12/2009 |
| WO | WO 2015/102642 A1 | 7/2015 |

OTHER PUBLICATIONS

Great Britain Search Report for Application No. GB1607814.9, dated Feb. 23, 2017, 5 pages.

* cited by examiner

ANTI-MICROBIAL COMPOSITIONS

FIELD

The present invention relates to compounds, compositions, methods and uses for sanitising and/or substantially removing biofilms and microorganisms living within or around said biofilm. In particular the invention relates to metal-EDTA compounds which can be used in wound treatments, wound dressings, medical devices, water treatments, food processing and dental care to treat biofilms and the pathogenic microorganisms which live within and around said biofilms.

BACKGROUND

The colonisation of surfaces (abiotic and biotic), including skin and medical devices, by microorganisms represents a significant infection risk to a patient. When these microorganisms attach and grow on a surface they form a biofilm. It is increasingly recognised that microbial populations living within a biofilm environment contribute to delayed healing and increased infection risk. For example, chronic wounds may fail to heal effectively if pathogenic biofilms are present. Such biofilms resist the patient's immune system and anti-microbial treatments which may lead to tissue breakdown, inflammation and/or serious infections. These wounds are often colonised by a polymicrobial population. In such chronic wounds the microorganisms within the biofilm can be 100 to 1000 times more tolerant to anti-microbial interventions compared to their planktonic counterparts (Singh and Barbul, Wound Rep Reg. 16:1, 2008). A recent study by James et al. (Wound Rep Reg. 16: 37-44, 2008) has shown that at least 60% of chronic wounds analysed in their study were colonised by biofilms.

For a biofilm to develop on a surface, be it a biotic or abiotic surface, microorganisms have to first attach themselves to the surface. Once securely attached to the surface they proliferate and produce extracellular polymeric substances (EPS). EPS is composed of polysaccharides, proteins, extracellular DNA and other biological and inorganic material. EPS forms the matrix of a biofilm and helps to protect microorganisms from immune cells and anti-microbial agents, reducing the efficacy of anti-microbial agents (e.g. antibiotics and biocides, in particular antiseptics). Therefore it is desirable to disrupt the biofilm and expose the microorganisms to anti-microbial agents applied to the biofilm and in doing so reduce the concentration of such anti-microbial agents needed to effectively treat the microorganisms living in the biofilm.

Ethylenediaminetetra-acetic acid (EDTA) added as the di-sodium or calcium di-sodium salts has been used to treat topical infections or to treat hard surfaces such as catheters. WO03/047341 describes the use of EDTA, for example as an additive for a toothpaste. EDTA is also used as a formulation agent to reduce the effects of water hardness and generally as a chelating agent.

EDTA combinations with other antibiotic agents have been disclosed, for example in U.S. Pat. No. 5,998,488 where EDTA is used in combination with an anti-microbial preservative in a solution for ophthalmic use.

SUMMARY OF THE INVENTION

Figure 1:
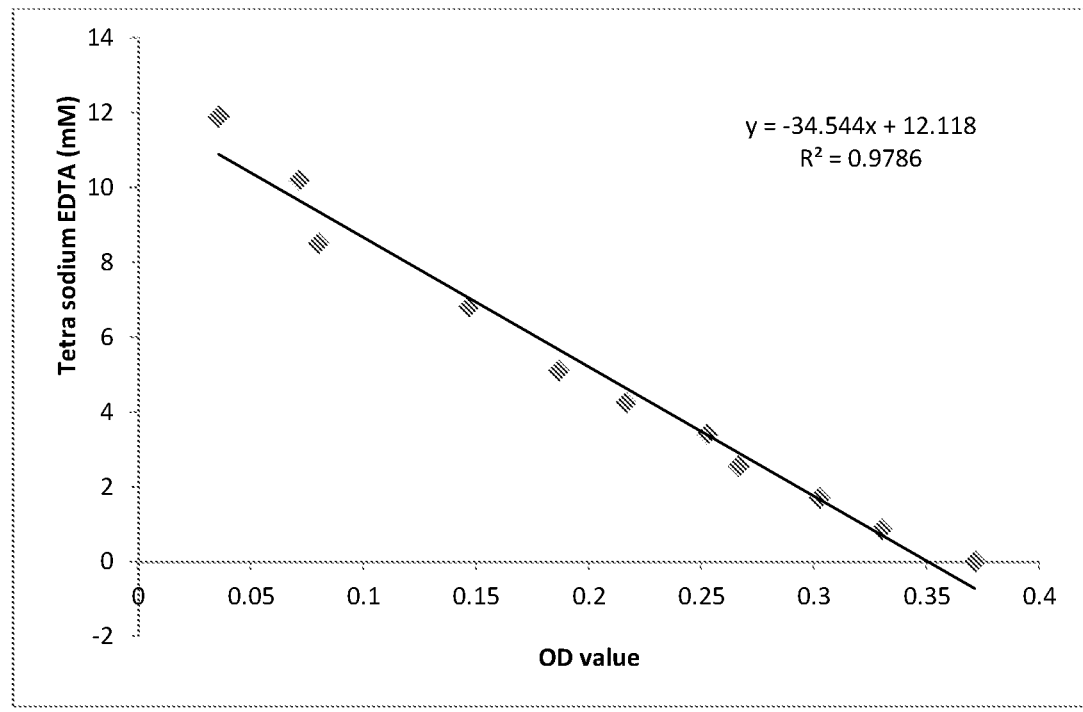
FIG. 1 shows the standard correlation curve for tetra sodium EDTA.

It is one aim of the present invention, amongst others, to provide a compound which addresses at least one disadvantage of the prior art, whether identified here or elsewhere, or to provide an alternative to existing anti-microbial agents, for example metal-EDTA compounds of the prior art. For instance it may be an aim of the present invention to provide a compound or composition which provides anti-biofilm and/or anti-microbial and/or anti-inflammatory activity in a wound treatment or a medical device.

According to aspects of the present invention, there is provided a compound, composition, product and use as set forth in the appended claims. Other features of the invention will be apparent from the dependent claims, and the description which follows.

Throughout this specification, the term "comprising" or "comprises" means including the component(s) specified but not to the exclusion of the presence of other components. The term "consisting essentially of" or "consists essentially of" means including the components specified but excluding other components except for materials present as impurities, unavoidable materials present as a result of processes used to provide the components, and components added for a purpose other than achieving the technical effect of the invention. Typically, when referring to compositions, a composition consisting essentially of a set of components will comprise less than 5% by weight, typically less than 3% by weight, more typically less than 1% by weight of non-specified components.

The term "consisting of" or "consists of" means including the components specified but excluding the addition of other components.

Whenever appropriate, depending upon the context, the use of the term "comprises" or "comprising" may also be taken to encompass or include the meaning "consists essentially of" or "consisting essentially of", and may also be taken to include the meaning "consists of" or "consisting of".

The optional features set out herein may be used either individually or in combination with each other where appropriate and particularly in the combinations as set out in the accompanying claims. The optional features for each aspect or exemplary embodiment of the invention as set out herein are also to be read as applicable to any other aspect or exemplary embodiments of the invention, where appropriate. In other words, the skilled person reading this specification should consider the optional features for each exemplary embodiment of the invention as interchangeable and combinable between different exemplary embodiments.

In this specification, the term "anti-microbial" refers to a compound or a composition that may kill and/or inhibit and/or stop the growth of any one or more types of microorganisms, including, viruses, prions, protozoa, amoeba, bacteria, fungi and yeasts, or any one or more of specific species of microorganism.

The term "biofilm" refers to both a monocultured and a polymicrobial community of microorganisms enclosed in an extracellular polymeric matrix (composed of EPS), and attached to a biotic or an abiotic surface.

The term "biofilm formation" refers to the attachment of microorganisms to surfaces and the subsequent development of multiple layers of cells within an EPS matrix.

The term "anti-biofilm" refers to the inhibition of microbial biofilm formation and/or disruption and/or dispersal of biofilms and/or detachment and/or dispersion and/or breakdown of EPS of a biofilm.

The term "anti-inflammatory" refers to the property of a substance or treatment that reduces inflammation or swelling, typically in a wound.

The term "infection" refers to the invasion and multiplication of microorganisms such as bacteria, viruses, fungi, yeasts and parasites that are not normally present within the body. An infection may cause no symptoms and be subclinical, or it may cause symptoms and be clinically apparent. An infection may remain localized, or it may spread through the blood or lymphatic vessels to become systemic (body wide). Microorganisms that live naturally in the body are not considered infections.

The term "wound" refers to a type of injury in which skin is torn, cut or punctured (an open wound), or where blunt force trauma causes a contusion (a closed wound).

The term "acute wound" refers to those wounds which are new and in the first phase of healing. Acute wounds are characterized by skin layers that have been punctured or broken by an external force or object. Any acute wound can progress to a chronic wound if it does not heal within the expected time frame or as a result of a poor supply of blood, oxygen, nutrients or through poor hygiene. Acute wounds should be properly treated to avoid infection and/or inflammation. Acute wounds are categorized based on causes such as lacerations, abrasions, punctures, incisions, gunshots, burns and according to their size and depth (superficial or deep).

The term "chronic wound" refers to a wound that will not repair itself over time. Chronic wounds are often thought to be "stuck" in one of the phases of wound healing, and are most often seen in the older adult population. Typically, if a wound is not healing as expected within 2-3 months, it is considered chronic. Chronic wounds include pressure ulcers (e.g. bed sores), arterial and venous leg ulcers, and diabetic ulcers.

According to a first aspect of the present invention, there is provided a compound of formula $M_n(EDTA)$; wherein:
 n is an integer from 2 to 4;
 each M is a metal ion; and
 $M_n$ comprises at least two different metal ions selected from Ag, Al, Au, Ba, Bi, Tl, Ce, Co, Cu, Fe, Ga, Ir, Mo, Rh, Ru, Ti, and Zn ions.

The compound of formula $M_n(EDTA)$ may be described as a metal-EDTA compound. The term "metal-EDTA compound" refers to any type of chemical species which comprises at least one metal and at least one EDTA molecule, whether said metal and said EDTA compound are present as salts, ions or neutral species and therefore encompasses metal-EDTA salts, chelates and co-ordination complexes. The compound of formula $M_n(EDTA)$ may be a salt and/or a chelate and/or a co-ordination complex. Suitably the compound of formula $M_n(EDTA)$ is a salt comprising ionic bonds between the metal atoms and the EDTA molecule. Suitably the compound of formula $M_n(EDTA)$ is a neutral compound. It may be assumed that where no charge information is given in a particular formula, the compound represented by that formula has no overall charge.

The compound may be in the form of a solid. Alternatively the compound may be present in a solution or a suspension, suitably an aqueous solution or an aqueous suspension, suitably an aqueous solution.

n is an integer from 2 to 4. Therefore the compound may be a di-metal-EDTA compound, a tri-metal-EDTA compound or a tetra-metal-EDTA compound.

The compound may be a mixture of compounds of formula $M_n(EDTA)$. The mixture of compounds of formula $M_n(EDTA)$ may comprise different numbers of metal ions, for example at least two of the following species: $M_2(EDTA)$, $M_3(EDTA)$ and $M_4(EDTA)$.

In compounds wherein the formula is $M_4(EDTA)$, each metal ion has a 1+ charge and the compound has no overall charge, the EDTA component has no free carboxylic acid groups. In compounds wherein the formula is $M_3(EDTA)$, each metal ion has a 1+ charge and the compound has no overall charge, the EDTA component has one free carboxylic acid group. In compounds wherein the formula is $M_2(EDTA)$, each metal ion has a 1+ charge and wherein the compound has no overall charge, the EDTA component has two free carboxylic acid groups. The number of metal ions (M) which the compound comprises may depend on the pH of a solution in which the compound may be present. For example an acidic pH may reduce the number of metal ions (M) present in the compound.

If any of the metal ions (M) present in the compound of formula $M_n(EDTA)$ have a higher than 1+ charge, for example $Zn^{2+}$ and wherein the compound has no overall charge, then the number of metal ions (M) which can be present in the compound is reduced (i.e. n is 2 or 3) and the number of free carboxylic acids present in the compound will be reduced accordingly.

$M_n$ comprises at least two different metal ions selected from Ag, Al, Au, Ba, Bi, Tl, Ce, Co, Cu, Fe, Ga, Ir, Mo, Rh, Ru, Ti, and Zn ions. Suitably $M_n$ comprises at least two different metal ions selected from Ag, Au, Ce, Cu, Ga and Zn ions.

As the compound has the formula $M_n(EDTA)$ and $M_n$ comprises at least two different metal ions selected from Ag, Al, Au, Ba, Bi, Tl, Ce, Co, Cu, Fe, Ga, Ir, Mo, Rh, Ru, Ti, and Zn ions, the compound may be considered to comprise EDTA, at least a first metal ion $M^1$ and at least a second metal ion $M^2$, wherein $M^1$ and $M^2$ are different and are each selected from Ag, Al, Au, Ba, Bi, Tl, Ce, Co, Cu, Fe, Ga, Ir, Mo, Rh, Ru, Ti, and Zn ions.

$M_n$ can comprise up to 4 metal ions. When n is 3 or 4, $M_n$ may comprise other metal ions in addition to the at least two different metal ions selected from Ag, Al, Au, Ba, Bi, Tl, Ce, Co, Cu, Fe, Ga, Ir, Mo, Rh, Ru, Ti, and Zn ions. In some embodiments the other metal ions which $M_n$ comprises are Na ions. For example when n=3 or 4 $M_n$ may comprise one Na ion or when n=4 $M_n$ may comprise two Na ions.

In some embodiments $M_n$ comprises only metal ions selected from Ag, Al, Au, Ba, Bi, Tl, Ce, Co, Cu, Fe, Ga, Ir, Mo, Rh, Ru, Ti, and Zn ions. For example $M_n$ may comprise two, three or four different metal ions selected from Ag, Al, Au, Ba, Bi, Tl, Ce, Co, Cu, Fe, Ga, Ir, Mo, Rh, Ru, Ti, and Zn ions. Alternatively $M_n$ may comprise more than one of any specific metal ion selected from Ag, Al, Au, Ba, Bi, Tl, Ce, Co, Cu, Fe, Ga, Ir, Mo, Rh, Ru, Ti, and Zn ions, for example more than one Ag ion.

Suitably n=3 or 4 and $M_n$ comprises two Ag ions. In this case, the compound of the formula $M_n(EDTA)$ also comprises at least one metal ion selected from Al, Au, Ba, Bi, Tl, Ce, Co, Cu, Fe, Ga, Ir, Mo, Rh, Ru, Ti, and Zn ions.

Suitably $M_n$ comprises at least one Ag ion. Suitably $M_n$ comprises at least one Ag ion and at least one metal ion selected from Cu, Ga and Zn ions. Suitably $M_n$ comprises at least two Ag ions and at least one metal ion selected from Cu, Ga and Zn ions.

Suitably $M_n$ comprises at least one Ag ion and one Zn ion. Suitably n is 3 and $M_n$ comprises two Ag ions and one Zn ion. Suitably the compound of this first aspect has the formula $Ag_2Zn(EDTA)$.

In some embodiments, n is 2 and $M_n$ comprises one Ag ions and one Zn ion. Suitably the compound of this first aspect has the formula AgZnNa(EDTA).

As an external entity to the body, a biofilm will cause the human body to initiate an inflammatory response where there is an up-regulation in immune processes. Zn ions have anti-inflammatory properties and therefore when the compound of the formula $M_n(EDTA)$ includes one or more Zn ions, the Zn ions may provide a beneficial anti-inflammatory effect to a wound on which the compound of this first aspect may be applied, in addition to any anti-microbial and/or anti-biofilm effects of the compound.

Suitably $M_n$ comprises at least one Ag ion and one Cu ion. Suitably n is 3 and $M_n$ comprises two Ag ions and one Cu ion. Suitably the compound of this first aspect has the formula $Ag_2Cu(EDTA)$.

In some embodiments, n is 2 and $M_n$ comprises one Ag ions and one Cu ion. Suitably the compound of this first aspect has the formula AgCuNa(EDTA).

Suitably n is 2 and $M_n$ comprises a Cu ion and a Zn ion. Suitably the compound has the formula CuZn(EDTA).

When $M_n$ comprises a Cu ion and a Zn ion, the Cu ions in combination with the Zn ions may exhibit a synergistic anti-microbial effect, which may allow a lower and therefore less cytotoxic concentration of a compound of this first aspect to be used than may otherwise be possible.

The compounds of this first aspect may be synthesised according to the methods described in the Examples. Generally, the compounds of this first aspect can be synthesised by reacting a tetra sodium salt of EDTA ($Na_4(EDTA)$), which is commercially available, with a mixture of salts of at least two different metal ions (M) selected from Ag, Al, Au, Ba, Bi, Tl, Ce, Co, Cu, Fe, Ga, Ir, Mo, Rh, Ru, Ti, and Zn ions. Examples of such salts include sulphates and chlorides.

The inventors have found that compounds of this first aspect may exhibit useful biological activity. The compounds may exhibit any one or more of anti-microbial, anti-biofilm and anti-inflammatory activities in use. The compounds are preferably safe for human administration and are biocompatible and non-corrosive. Suitably the compounds exhibit anti-microbial and/or anti-biofilm and/or anti-inflammatory activities in use, for example when incorporated into a wound dressing or a medical device.

The compounds of this first aspect may be useful in treating or combatting biofilms, for example disrupting and/or dispersing biofilms and providing an anti-microbial action on the microbes living on and within said biofilm and/or breaking down the EPS of the biofilm. The compounds of this first aspect may be used in a wound dressing, a medical device, on skin or on other abiotic or biotic surfaces important in water treatment (including water storage and distribution), food preparation and processing or dentistry. In some embodiments, the compounds of this first aspect may be used in the form of a solution or suspension, for example for decontaminating surfaces, food preparation and processing equipment and/or food products, in particular meat processing equipment and meat products. Such a solution may be used as a mastitis dip solution, an ophthalmic solution, for wound irrigation or in dentistry. For example, the compounds of this first aspect may be used in an endodontic irrigating solution and/or for cleaning/disinfecting dental water lines.

In some embodiments, the compounds of this first aspect may be used as a medicament, for example in a cream, paste or lotion.

Without being bound by theory, the use of compounds according to the first aspect when applied to a wound, for example when the compound is incorporated into a wound dressing, may react with Ca and/or Mg ions present in a biofilm associated with the wound. This reaction may remove the Ca and/or Mg ions from the biofilm which then disrupts the integrity of the biofilm. It is believed that Ca and Mg ions are important for the maintenance of a biofilm's structural integrity as these ions bind together the EPS which makes up the matrix of the biofilm. This reaction may also cause the metal ions (M) to be displaced from the compound and therefore be released into the wound and/or biofilm to produce desirable biological activity. For example, if the metal ions (M) of the compound comprise Ag and Zn ions, the reaction with the Ca and/or Mg present in a biofilm may release Ag ions into the wound and/or biofilm to provide a beneficial anti-microbial effect and/or may release Zn ions into the wound and/or biofilm to provide a beneficial anti-inflammatory effect. Zn ions are believed to provide an anti-inflammatory effect. The use of the compound of this first aspect may therefore improve wound healing by simultaneously preventing and treating microbial infections and/or reducing wound inflammation.

According to a second aspect of the present invention there is provided a composition comprising one or more compounds of formula $M_n(EDTA)$ according to the first aspect.

The compound of formula $M_n(EDTA)$ in the composition of the second aspect may have any of the suitable features and/or advantageous properties described herein in relation to the first aspect.

The composition of this second aspect may be provided in any suitable form, such as in the form of a solution or a suspension or in a dry form.

Suitably the composition is a fluid.

The composition may be an aqueous solution, a lotion, a cream, a balm, a gel, a paste or a solid, suitably powdered, composition.

In some embodiments, the composition of this second aspect is a solution of the compound of formula $M_n(EDTA)$. In such solutions, the compound of formula $M_n(EDTA)$ is suitably dissolved in a suitable solvent. The solution may comprise an aqueous solution such as water or saline, or another biocompatible solution in which the compound of formula $M_n(EDTA)$ is soluble. The solution may comprise an alcohol, for example ethanol.

In one embodiment, the composition is a solution of the compound of formula $M_n(EDTA)$ in a mixture of water and ethanol. Such solutions may be highly efficacious and may be prepared by making a concentrated stock solution of the compound of formula $M_n(EDTA)$ in water and then introducing the desired concentration of ethanol.

The solution of the compound of formula $M_n(EDTA)$ is preferably provided in a sterile and non-pyrogenic form and may be packaged in any convenient fashion.

In some embodiments, the solution of the compound of formula $M_n(EDTA)$ may be provided in connection with or as part of a medical device, such as in a pre-filled syringe or another medical device. The solution of the compound of formula $M_n$(EDTA) may be prepared under sterile, aseptic conditions, or may be sterilized following preparation and/or packaging using any of a variety of suitable sterilization techniques. Single use vials, syringes or containers of the solution of the compound of formula $M_n$(EDTA) may be provided. Multiple use vials, syringes or containers may also be provided.

In some embodiments, the composition of this second aspect is provided in a substantially dry form, such as a substantially dry coating on a surface of tubing, or a conduit, or a medical or industrial device such as a catheter or a container and the like. Such substantially dry forms of the composition of this second aspect may be provided in a powder or lyophilized form that may be reconstituted to form a solution with the addition of a solvent. Substantially dry forms of the composition may alternatively be provided as a coating, or may be incorporated in a gel or another type of carrier, or encapsulated or otherwise packaged and provided on a surface as a coating or in a container. Such substantially dry forms of the composition of this second aspect are formulated such that in the presence of a solvent, the substantially dry composition forms a solution or suspension of the compound of formula $M_n$(EDTA) having the properties described above. In certain embodiments, different encapsulation or storage techniques may be employed such that effective time release of the compound of formula $M_n$(EDTA) is accomplished upon extended exposure to solutions. In this embodiment, the substantially dry composition of this second aspect may provide anti-microbial and/or anti-biofilm and/or anti-inflammatory activity over an extended period of time and/or upon multiple exposures to solutions.

Suitably the composition is an aqueous solution.

Suitably the pH of the composition is up to 12.5. Suitably the pH of the composition is in the range from 4.0 to 12.0, suitably in the range from 4.0 to 10.0, suitably from 4.5 to 8.0. Suitably the pH of the composition is in the range from 4.0 to 7.0, suitably in the range from 4.0 to 6.0, suitably from 4.0 to 5.0.

Suitably the composition is an aqueous solution having a pH in the range from 4.0 to 12.0, suitably in the range from 4.0 to 11.0, suitably in the range from 4.0 to 10.0, suitably from 4.5 to 8.0. Suitably the pH of the composition is in the range from 4.0 to 7.0, suitably in the range from 4.0 to 6.0, suitably from 4.0 to 5.0.

Suitably the compound of formula $M_n$(EDTA) is present in the composition in an amount of at least 0.01 ppm, suitably at least 0.1 ppm, suitably at least 1.0 ppm, suitably at least 10 ppm, suitably at least 100 ppm, suitably at least 1,000 ppm, suitably at least 5,000 ppm.

Suitably the compound of formula $M_n$(EDTA) is present in the composition in an amount of up to 100,000 ppm, suitably up to 10,000 ppm, suitably up to 5,000 ppm.

Suitably the compound of formula $M_n$(EDTA) is present in the composition in an amount of from 0.01 ppm to 100,000 ppm, suitably from 0.1 ppm to 10,000 ppm, suitably from 1.0 ppm to 10,000 ppm, suitably from 10 ppm to 100 ppm, suitably from 100 ppm to 10,000 ppm, suitably from 1,000 ppm to 10,000 ppm.

As a result of the presence of the compound of formula $M_n$(EDTA) in the composition, the composition comprises EDTA and at least a first metal ion $M^1$ and a second metal ion $M^2$, wherein $M^1$ and $M^2$ are different and are each selected from Ag, Al, Au, Ba, Bi, Tl, Ce, Co, Cu, Fe, Ga, Ir, Mo, Rh, Ru, Ti, and Zn ions.

Suitably EDTA is present in the composition in an amount of from at least 0.01 ppm, suitably at least 0.1 ppm, suitably at least 1.0 ppm, suitably at least 10 ppm, suitably at least 100 ppm, suitably at least 1,000 ppm.

Suitably EDTA is present in the composition in an amount of up to 100,000 ppm, suitably up to 10,000 ppm, suitably up to 5,000 ppm.

Suitably EDTA is present in the composition in an amount of from 0.01 ppm to 100,000 ppm, suitably from 0.1 ppm to 10,000 ppm, suitably from 1.0 ppm to 10,000 ppm, suitably from 10 ppm to 100 ppm, suitably from 100 ppm to 10,000 ppm, suitably from 1,000 ppm to 10,000 ppm.

Suitably the first metal ion $M^1$ is present in the composition in an amount of from at least 0.01 ppm, suitably at least 0.1 ppm, suitably at least 1.0 ppm, suitably at least 10 ppm, suitably at least 100 ppm, suitably at least 1,000 ppm.

Suitably the first metal ion $M^1$ is present in the composition in an amount of up to 100,000 ppm, suitably up to 10,000 ppm, suitably up to 5,000 ppm.

Suitably the first metal ion $M^1$ is present in the composition in an amount of from 0.01 ppm to 100,000 ppm, suitably from 0.1 ppm to 10,000 ppm, suitably from 1.0 ppm to 10,000 ppm, suitably from 10 ppm to 100 ppm, suitably from 100 ppm to 10,000 ppm, suitably from 1,000 ppm to 10,000 ppm.

Suitably the second metal ion $M^2$ is present in the composition in an amount of from at least 0.01 ppm, suitably at least 0.1 ppm, suitably at least 1.0 ppm, suitably at least 10 ppm, suitably at least 100 ppm, suitably at least 1,000 ppm.

Suitably the second metal ion $M^2$ is present in the composition in an amount of up to 100,000 ppm, suitably up to 10,000 ppm, suitably up to 5,000 ppm.

Suitably the second metal ion $M^2$ is present in the composition in an amount of from 0.01 ppm to 100,000 ppm, suitably from 0.1 ppm to 10,000 ppm, suitably from 1.0 ppm to 10,000 ppm, suitably from 10 ppm to 100 ppm, suitably from 100 ppm to 10,000 ppm, suitably from 1,000 ppm to 10,000 ppm.

The suitable concentration of the first and/or second and/or any further metal ion may depend on the specific metal ion present. For example, a silver metal ion may be present in a relatively low concentration and still be effective in a given application.

The composition may comprise other metal ions in addition to the at least two different metal ions selected from Ag, Al, Au, Ba, Bi, Tl, Ce, Co, Cu, Fe, Ga, Ir, Mo, Rh, Ru, Ti, and Zn ions.

Such other metal ions may be any suitable metal ion, for example Na ions.

The composition may comprise more than two different metal ions selected from Ag, Al, Au, Ba, Bi, Tl, Ce, Co, Cu, Fe, Ga, Ir, Mo, Rh, Ru, Ti, and Zn ions.

The composition may comprise a carrier and/or an excipient, suitably a pharmaceutically acceptable carrier and/or excipient. Suitable carriers and/or an excipients may be selected from water, ethanol, polypropylene glycol, glycerol, sorbitol, hydrocolloids, polyoxyethylene block copolymers, carboxy methyl cellulose, pluronic F-127, cotton, chitosan, silicone, polyurethanes, acrylics, hydrogels, bamboo, soya, oils/fats, micelles, emulsions, paints, sodium alginate, polyethylene glycol, thickening agents such as Carbopol™ and mixtures thereof.

The composition of this second aspect may be in the form of a water-based gel. Suitably the composition is a hydrogel which comprises the one or more compounds of formula $M_n$(EDTA). Suitably such hydrogels can maintain a moist wound healing environment and promote wound healing when said composition is applied to a wound, for example as part of a wound dressing. Such hydrogels may flow into the wound when applied to said wound to form an intimate contact with the wound bed and provide anti-microbial and/or anti-inflammatory effects to the whole wound. Suitably the hydrogel has a high enough viscosity that it does not flow out of wounds on areas of the body that are or become non-horizontal through movement of the patient. Suitably the hydrogel comprises a buffer, suitably to buffer the pH of the hydrogel to between 5.5 to 12.0. Suitable buffers are known in the art.

The composition may comprise a non-metal ion anti-microbial agent.

Suitable non-metal ion anti-microbial agents may be selected from any one or more of a chlorhexidine, a chlorhexadine salt, a triclosan, a polymoxin, a tetracycline, an amino glycoside (e.g. gentamicin or Tobramycin™), a rifampicin, a bacitracin, an erythromycin, a neomycin, a chloramphenicol, a miconazole, a quinolone, a penicillin, a nonoxynol 9, a fusidic acid, a cephalosporin, a mupirocin, a metronidazole, a secropin, a protegrin, a bacteriolcin, a defensin, a nitrofurazone, a mafenide, a acyclovir, a vanocmycin, a clindamycin, a lincomycin, a sulfonamide, a norfloxacin, a pefloxacin, a nalidizic acid, an oxalic acid, an enoxacin acid, a ciprofloxacin, a biguanide, iodine, tea tree oil, honey and superoxides. In one embodiment the anti-microbial agent comprises polyhexamethylene biguanide (PHMB) and/or derivatives thereof.

The non-metal ion anti-microbial agent may provide a beneficial anti-microbial which is additive to and/or synergistic with any anti-microbial effect provided by the compound of formula $M_n(EDTA)$.

The composition may comprise a surfactant.

A suitable surfactant may be sodium hexametaphosphate or a quaternary ammonium compound. A surfactant may improve the anti-biofilm effectiveness of the composition by removing matter from a biofilm during and/or after the action of the compound of formula $M_n(EDTA)$ to disrupt the biofilm. For example, the compound of formula $M_n(EDTA)$ may act to disrupt the biofilm and in doing so produce flocculated cells. The surfactant may act to at least partially solubilise and remove these cells and prevent them from re-adhering to the biofilm and in doing so assist with the break-up and removal of the biofilm.

The composition may comprise an anti-biofilm agent, suitably in addition to any anti-biofilm properties of the compound of formula $M_n(EDTA)$ and/or any non-metal ion anti-microbial agent, if present, and/or any surfactant, if present. The composition may comprise an anti-biofilm agent selected from any one or more of DisperinB, DNase 1, ethylene glycol tetraacetic acid (EGTA), Proteinase K, apyrase, cis-2-decenoic acid, alginate lyase, lactoferrin, gallium, cellulose, and 5-fluorouracil.

In some embodiments, the composition comprises fibres which are in contact with the one or more compounds of formula $M_n(EDTA)$.

Such compositions comprising fibres may be formed by impregnating the composition into and/or coating the composition onto fibres. Suitable fibres may be selected from natural fibres, synthetic fibres and combinations thereof. Suitable fibres may be selected from any one or more fibres of cellulose, alginates, cotton, chitosan, soya, bamboo, carboxymethylcellulose, Rayon, Nylon, acrylic, polyester, polyurethane, polyurethane foam and combinations thereof.

Such compositions comprising fibres may be incorporated into and/or used to form a wound dressing. Such a wound dressing may have the advantage that the one or more compounds of formula $M_n(EDTA)$ present in the composition are delivered to the wound, producing the beneficial effects referred to in relation to the first aspect. For example, the wound dressing may exhibit any one or more of anti-microbial, anti-biofilm and anti-inflammatory activities in use and therefore promote wound healing whilst combatting infection, if present.

According to a third aspect of the present invention there is provided a wound dressing comprising a compound according to the first aspect or a composition according to the second aspect.

The wound dressing may have any of the suitable features and advantages described in relation to the first and second aspects.

Suitably the wound dressing comprises the compound of formula $M_n(EDTA)$ in a wound contact layer which has been impregnated, coated, dipped, laminated and/or sprayed with the compound of formula $M_n(EDTA)$. Alternatively or additionally the wound dressing may comprise the compound of formula $M_n(EDTA)$ in an absorbent layer that is attached to a wound contact layer. Alternatively or additionally the wound dressing may comprise the compound of formula $M_n(EDTA)$ in adhesive which contacts the skin in use.

According to a fourth aspect of the present invention there is provided a medical device comprising a compound according to the first aspect or a composition according to the second aspect.

The medical device may be a catheter. In some embodiments the medical device may be an intubation tube. The medical device may be a medical tube, a conduit, an intravascular device, an implanted medical device, a medical or veterinary instrument, a contact lens, an optical implant or a dental, orthodontic or periodontal device.

Suitably the compound according to the first aspect or the composition according to the second aspect is coated onto at least a part of a surface of the medical device, suitably a surface which is intended to contact a part of a patient's body, in use. Methods of coating the compound or composition onto such a surface are known in the art.

Suitably the medical device of this fourth aspect has a reduced capacity for biofilm formation than a comparable medical device of the prior art which does not comprise such a compound or composition. The medical device of this fourth aspect may therefore reduce or substantially prevent infections caused by biofilm formation and pathogenic microorganism growth on the medical device.

According to a fifth aspect of the present invention there is provided a use of a compound according to the first aspect or a composition according to the second aspect to sanitise and/or substantially remove a biofilm from a substrate.

Alternatively and/or additionally there is provided a method of sanitising and/or substantially removing a biofilm from a substrate, the method comprising treating the substrate with a compound according to the first aspect or a composition according to the second aspect.

The substrate may be any surface where biofilm treatment and/or removal is required. The substrate may be a wound on a human or animal body, the wound being of any of the types described above. The substrate may be a part of a medical device. In some embodiments the substrate may be a part of food preparation and processing equipment or a food product, for example meat processing equipment or meat products.

Suitably the use and/or method at least disrupts and/or disperses the biofilm. Suitably the use and/or method increases the susceptibility of the biofilm and the microorganisms within it to attack by the compound of the first aspect and/or any metal ions released from the compound and/or any additional agents (such as non-metal ion antimicrobial agents and/or anti-biofilm agents) present in the composition according to the second aspect. Suitably the use and/or method completely removes the biofilm from the substrate. Suitably the use and/or method sanitises the substrate. Suitably the use and/or method completely removes the biofilm from the substrate and sanitises the substrate.

The use and/or method carried out on a wound may advantageously facilitate wound healing and/or treat infections and/or reduce inflammation.

The use and/or method carried out on a medical device may advantageously clean and/or sanitise the medical device and therefore prevent infections caused by medical devices comprising biofilms harbouring pathogenic microorganisms.

The use and/or method carried out on a food product may advantageously slow or preferably stop the growth of pathogenic microorganisms on the food product and therefore prevent spoilage of the food product and food poisoning which may result from ingesting such food contaminated with pathogenic microorganisms.

According to a sixth aspect of the present invention there is provided a compound according to the first aspect or a composition according to the second aspect for use as a medicament.

Suitably the compound or composition is for use to sanitise and/or substantially remove a biofilm from a wound.

The compound or composition for use in the sixth aspect may be used to treat infections of cuts, bruises, surgical sites, lacerations, abrasions, punctures, incisions, gunshots, burns, pyoderma, atopic dermatitis, eczema, pressure ulcers, venous and artery leg ulcers, diabetic foot ulcers, cystic fibrosis (CF)-associated infections, mastitis, otitis, community or hospital acquired infections or food-borne diseases.

According to a seventh aspect of the present invention there is provided a method of producing a compound of the first aspect, the method comprising reacting a metal-EDTA compound with a salt of a first metal ion selected from Ag, Al, Au, Ba, Bi, Tl, Ce, Co, Cu, Fe, Ga, Ir, Mo, Rh, Ru, Ti, and Zn ions and a salt of a second metal ion selected from Ag, Al, Au, Ba, Bi, Tl, Ce, Co, Cu, Fe, Ga, Ir, Mo, Rh, Ru, Ti, and Zn ions; wherein the first and second metal ions are different.

Suitably the method involves reacting the metal-EDTA complex with the salt of the first metal ion and the salt of the second metal ion at the same time.

In alternative embodiments, the method of this seventh aspect comprises the steps of:

a) reacting a metal-EDTA complex with a salt of a first metal ion selected from Ag, Al, Au, Ba, Bi, Tl, Ce, Co, Cu, Fe, Ga, Ir, Mo, Rh, Ru, Ti, and Zn ions; and b) reacting the EDTA complex comprising one metal ion selected from Ag, Al, Au, Ba, Bi, Tl, Ce, Co, Cu, Fe, Ga, Ir, Mo, Rh, Ru, Ti, and Zn ions formed in step a) with a salt of a second metal ion selected from Ag, Al, Au, Ba, Bi, Tl, Ce, Co, Cu, Fe, Ga, Ir, Mo, Rh, Ru, Ti, and Zn ions;

wherein the first and second metal ions are different.

Suitably the steps of the method are carried out in the order step a) followed by step b).

According to a seventh aspect of the present invention there is provided a kit comprising a compound according to the first aspect or a composition according to the second aspect and a medical device or wound dressing.

Suitably the kit comprises a solution or suspension of the compound of formula $M_n(EDTA)$, suitably contained in a pre-filled syringe or another medical device.

Suitably the medical device is a catheter or an intubation tube.

According to an eighth aspect of the present invention there is provided a use of a compound according to the first aspect or a composition according to the second aspect to coat at least a part of a medical device.

According to a further aspect of the present invention there is provided a use of a compound according to the first aspect or a composition according to the second aspect in a wound dressing.

According to a further aspect of the present invention there is provided a use of a compound according to the first aspect or a composition according to the second aspect in a method of water treatment.

According to a further aspect of the present invention there is provided a use of a compound according to the first aspect or a composition according to the second aspect in a method of food preparation or food processing.

According to a further aspect of the present invention there is provided a use of a compound according to the first aspect or a composition according to the second aspect in a dental procedure.

According to a ninth aspect of the present invention there is provided a use of a compound according to the first aspect or a composition according to the second aspect to provide anti-biofilm and/or anti-microbial and/or anti-inflammatory activity in a wound treatment or a medical device.

According to a further aspect of the present invention there is provided a compound, composition, wound dressing, medical device or use substantially as described herein, and/or a compound, composition, wound dressing, medical device or use substantially as described herein with reference to the accompanying Figures and/or a compound, composition, wound dressing, medical device or use substantially as shown in the accompanying Figures.

EXAMPLES

Comparative Example 1—Tetra Silver—EDTA Formation and Elution

Standard Curve
Principle:

$Fe^{3+}$ reacts with thiocyanate producing red complexes. $Na_4(EDTA)$ (tetra sodium EDTA) reacts with the $Fe^{3+}$ resulting in a red colour that decreases as the levels of $Na_4EDTA$ increase.

Instrument:
UV spectrophotometer

Reagents:
$Na_4(EDTA)$ standard,
hydrochloric acid (HCl) ACS reagent,
thiocyanate solution—ammonium thiocyanate in 100 ml water,
$Fe^{3+}$ solution—formed by dissolving ammonium iron(III) sulfate dodecahydrate in a small amount of HCl, adding sodium acetate buffer and then adding to water.

TABLE 1

| Results | |
|---|---|
| Optical Density | $Na_4EDTA$ concentration (mM) |
| 0.3715 | 0 |
| 0.33 | 0.85 |

TABLE 1-continued

| Results | |
|---|---|
| Optical Density | Na$_4$EDTA concentration (mM) |
| 0.3025 | 1.7 |
| 0.2665 | 2.55 |
| 0.2525 | 3.4 |
| 0.2165 | 4.25 |
| 0.1865 | 5.1 |
| 0.1465 | 6.8 |
| 0.08 | 8.5 |
| 0.0715 | 10.2 |
| 0.0355 | 11.9 |
| 0.0365 | 13.6 |

FIG. 1 shows the standard correlation curve for tetra sodium EDTA. The results show there was a linear correlation between OD (optical density) value and the amount of tetra sodium EDTA in the solution at concentration from 0 to 11.9 mM, which means this method can be used to measure quantitatively tetra sodium EDTA as solid or in the solution.

Tetra Silver—ETDA Development and Elution Measurement

Methods
1. Prepare a polyurethane (PU) solution by dissolving 1 g PU in 10 ml dimethylformamide (DMF) at 60° C. overnight.
2. Prepare a tetra silver EDTA complex and suspend in the PU solution at different concentrations—100 mg/ml, 50 mg/ml, 10 mg/ml, 1 mg/ml and 0 mg/ml.
3. Coat the tetra silver EDTA on glass coverslips and plastic discs to make films.
4. The coated coverslips and plastic discs are then immersed in 2 ml deionized water for 1 week.
5. The elution of tetra silver EDTA is determined according to the standard curve method.

Results

The PU films on glass coverslips, were named G1, G2, G3, G4, and G5 correlating to different concentrations of tetra silver EDTA complex. The elution results are shown in table 2 below.

TABLE 2

| Films | Tetra silver-EDTA eluted (μg) eluted-% eluted |
|---|---|
| G1 (10 mg) | 3560.822-35.61 |
| G2 (5 mg) | 1755.496-35.11 |
| G3 (1 mg) | 358.2583-35.83 |
| G4 (0.1 mg) | 31.86451-31.86 |
| G5 | 0 |

The results indicated that after one week immersed in deionised water, about 30%-36% tetra silver EDTA eluted from the films.

Comparative Example 2—Ag$_4$(EDTA

Synthesis: 

Silver nitrate was reacted with a tetra-sodium salt of EDTA in a 4:1 molar ratio under vigorous stirring. The resulting solid was filtered off, washed with cold deionized water 3 times, washed with 50% ethanol, 70% ethanol and 100% ethanol one time each; and then dried in a vacuum oven at 50° C. in a dark flask to avoid exposure to direct light. A white powder of Ag$_4$(EDTA) was produced in the following yield.

| | | | Ag$_4$(EDTA) (s) | |
|---|---|---|---|---|
| | AgNO$_3$ | Na$_4$(EDTA) | Theory | Measured |
| Weight (g) | 0.680 | 0.380 | 0.720 | 0.605 |

Figure 2A:
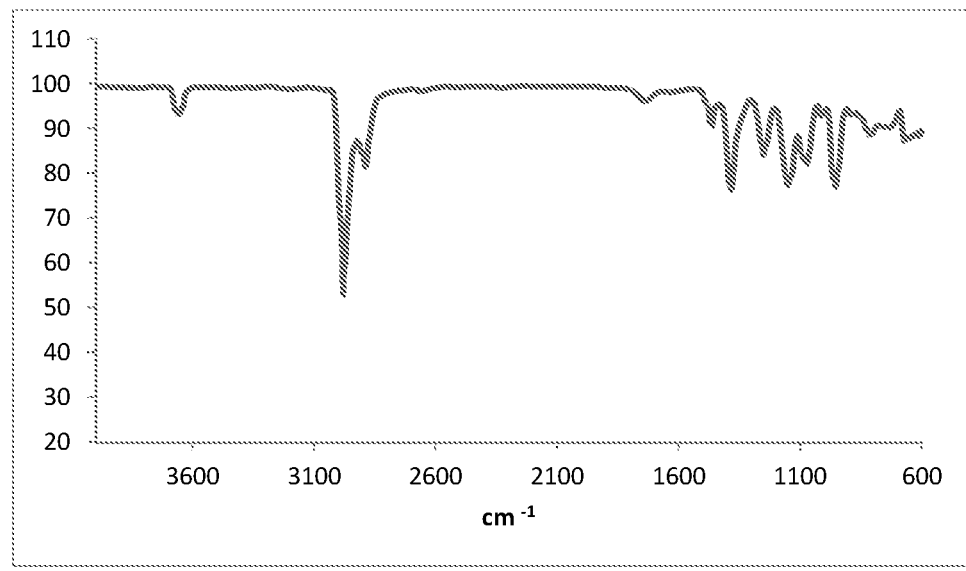
FIG. 2A-C shows the FTIR of (FIG. 2A) EDTA, (FIG. 2B) $Na_4(EDTA)$ and (FIG. 2C) $Ag_4(EDTA)$.
Figure 2B:
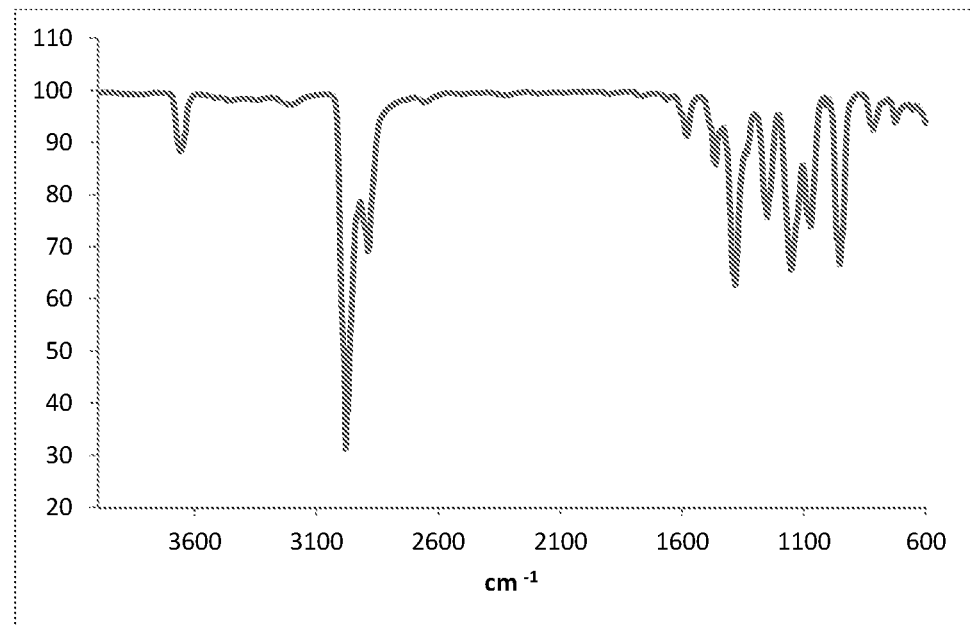
Figure 2C:
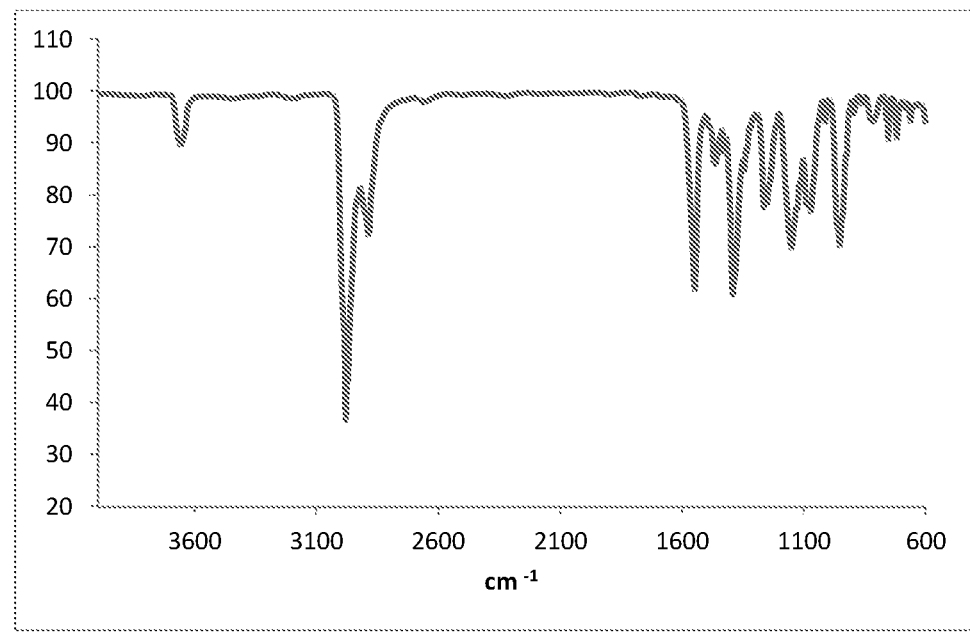

The FTIR of EDTA, Na$_4$(EDTA) and Ag$_4$(EDTA) are shown in FIGS. 2A-C. The absorption band centred at 1740 cm$^{-1}$ in FIG. 2A (EDTA) attributed to the stretching vibration of carbonyl in COOH is not present in the spectra of FIGS. 2B and 2C (Na$_4$EDTA and Ag$_4$EDTA respectively). The spectrum of the pure Na$_4$(EDTA) (FIG. 2B) is characterized by an absorption band centred at around 1580 cm$^{-1}$ which is attributed to the asymmetric stretching vibration of carbonyl in the four ionic carboxylate groups ($v_{as\ COO^-}$). The corresponding symmetric stretching vibration occurs close to 1465 cm$^{-1}$ ($v_{s\ COO^-}$). The asymmetric stretching vibration adsorption band of carbonyl in the Ag$_4$EDTA (FIG. 2C) is much stronger than the respective peak in Na$_4$EDTA and the band centre moves to around 1550 cm$^{-1}$. The corresponding symmetric stretching vibration band centred at 1465 cm$^{-1}$, which is a less intense absorption band than the one at 1550 cm$^{-1}$. The results indicated Ag$_4$EDTA complex formed.

Ag$_4$(EDTA) Suspension Coating Process

The Ag$_4$(EDTA) powders were suspended in deionised water at 1 mg/ml. A 100 μl portion of the suspension was dropped onto a first glass coverslip. A 50 μl portion of the suspension was added to a 50 μl portion of a 1.7% NaCl solution and dropped onto a second glass coverslip. A 50 μl portion of the suspension was mixed with a 50 μl portion of a PU solution and then dropped onto a third glass coverslip. All the coverslips were dried in vacuum oven at 50° C. in a dark flask to avoid exposure to direct light. The results showed that Ag$_4$(EDTA) can be coated on glass or as films of polymers (certainly at least polyurethane).

Displacement Experiment

Adding saline to the suspension of Ag$_4$(EDTA), the suspension quickly precipitated a solid (AgCl). The precipitate was filtered off, washed with deionized water 4 times; and then dried in a vacuum oven at 50° C. in a dark flask to avoid exposure to direct light.

| | | | AgCl (g) | |
|---|---|---|---|---|
| | Ag$_4$(EDTA) (g) | Saline | Theory | Measured |
| Weight (g) | 0.1277 | 5 ml | 0.1660 | 0.1784 |

Examples—Silver and Copper EDTA Complex Synthesis—Compounds 1 and 2

These compounds were prepared by first dissolving 38 g of ethylenediaminetetraacetic acid tetrasodium salt hydrate (Tetra sodium EDTA) in 1000 ml H$_2$O to provide solution 1. Then 68 g of silver nitrate (AgNO$_3$) was dissolved in 1000 ml H$_2$O to provide solution 2. 25 g of cupric sulfate pentahydrate (CuSO$_4$.5H$_2$O) was dissolved in 1000 ml H$_2$O to provide solution 3.

Preparation of Compound 1—AgCuNaEDTA 40 ml of solution 1 was mixed with 20 ml of solution 2 with vigorous stirring for 10 mins. The mixture was then filtered to obtain a solid. The solid was washed with water twice. About 60 ml of solution 3 was added to the solid and the mixture stirred vigorously until the solid totally dissolved.

The resultant solution was filtered with a 0.45 μm syringe filter to provide the product compound 1—AgCuNaEDTA.

Figure 3:
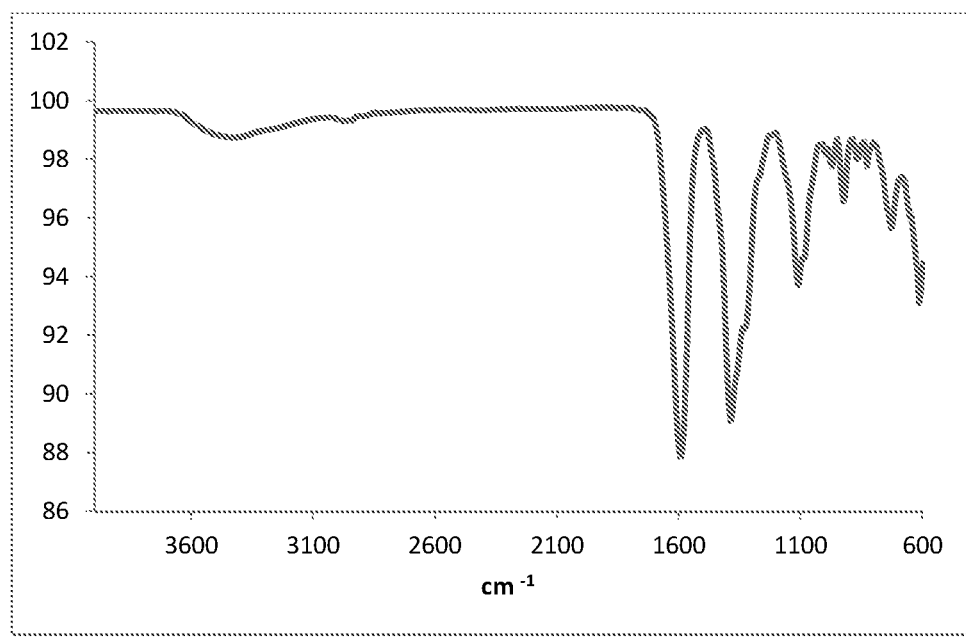
FIG. 3 shows the ATR-FTIR spectrum of the dark blue powder of $Ag_2Cu(EDTA)$.

Preparation of Compound 2—Ag$_2$CuEDTA 30 ml of solution 1 was mixed with 30 ml solution 2 with vigorous stirring for 10 mins. The mixture was then filtered to obtain a solid. About 80 ml of solution 3 was added to the solid and the mixture stirred vigorously until the solid totally dissolved. The resultant solution was filtered with a 0.45 μm syringe filter to provide the product compound 2—Ag$_2$CuEDTA. FIG. 3 shows the ATR-FTIR spectrum of the dark blue powder of Ag$_2$Cu(EDTA).

Examples—Silver and Zinc EDTA Complex Synthesis—Compounds 3 and 4

These compounds were prepared by first dissolving 38 g of ethylenediaminetetraacetic acid tetrasodium salt hydrate (Tetra sodium EDTA) in 1000 ml H$_2$O to provide solution 1. Then 68 g of silver nitrate (AgNO$_3$) was dissolved in 1000 ml H$_2$O to provide solution 2. 18.6 g of zinc sulfate monohydrate (ZnSO$_4$—H$_2$O) was dissolved in 1000 ml H$_2$O to provide solution 4.

Preparation of Compound 3—AgZnNaEDTA 40 ml of solution 1 was mixed with 20 ml solution 2 with vigorous stirring for 10 mins. The mixture was then filtered to obtain a solid. The solid was washed with water four times. About 100 ml of solution 4 was added to the solid and the mixture stirred vigorously until the solid totally dissolved. The resultant solution was filtered with a 0.45 μm syringe filter to provide the product compound 3—AgZnNaEDTA.

Preparation of Compound 4—Ag$_2$ZnEDTA 30 ml of solution 1 was mixed with 30 ml solution 2 with vigorous stirring for 10 mins. The mixture was then filtered to obtain a solid. About 120 ml of solution 4 was added to the solid and the mixture stirred vigorously until the solid totally dissolved. The resultant solution was filtered with a 0.45 μm syringe filter to provide the product compound 4—Ag$_2$ZnEDTA.

All compounds 1-4 were stored at room temperature in the dark as a precaution.

The following experiments were carried out with the following EDTA compounds/complexes prepared as described above:

Compound 1—AgCuNaEDTA
Compound 2—Ag$_2$CuEDTA
Compound 3—AgZnNaEDTA
Compound 4—Ag$_2$ZnEDTA Displacement Profiles of EDTA Complexes The displacement experiment described above was repeated for compounds 1-4 to provide the percent of the displacement of silver, copper, zinc from the EDTA complexes by physiological saline. The results are shown in Table 3 below.

TABLE 3

| EDTA compound | Displacement (%) | | |
|---|---|---|---|
| | Silver | Copper | Zinc |
| 1 | 81.37 ± 4.29 | 53.49 ± 5.56 | — |
| 2 | 77.99 ± 3.90 | 41.37 ± 6.92 | — |
| 3 | 82.32 ± 5.63 | — | 47.33 ± 13.29* |
| 4 | 80.77 ± 6.45 | — | 38.86 ± 9.01* |

The results of displacement experiments demonstrated that silver, copper and zinc form compounds 1-4 can be displaced by physiological saline (sodium ions). The results (Table 3) showed that about 80% silver, 40-50% copper and zinc were displaced by the sodium in the saline.

Incorporation of EDTA Complexes into Collagen

The EDTA compounds 1-4 were added to collagen films and then investigated for elution of these complexes. The collagen film was prepared from a solution of oxidized bovine atelocollagen type I, glycerol and EDTA compounds 1-4. 1.8 ml 10% glycerol solution was added into 20 ml oxidized bovine atelocollagen type I solution. 5 ml EDTA complex were added into the solution with vigorous stirring, and the mixture was adjusted to pH=7.0 by dropwise addition of 5% NaOH. The final solution was adjusted to 30 ml by ultrapure water and was cast into PVC mould. The solution was dried in a fume hood overnight. All the collagen films, impregnated with the EDTA complexes were immersed in water, saline or simulated wound fluid.

TABLE 4

Elution profile of EDTA compound 4 from collagen platform in water and saline

| Time | Elution in water (ppm) | | | Elution in saline (ppm) | | |
|---|---|---|---|---|---|---|
| (days) | Silver | Zinc | EDTA | Silver | Zinc | EDTA |
| 1 | 19.08 ± 0.92 | 9.86 ± 0.39 | 9.25 ± 0.90 | 20.34 ± 1.42 | 5.65 ± 0.06 | 9.75 ± 1.31 |
| 2 | 12.61 ± 1.04 | 9.60 ± 0.33 | 0.96 ± 0.64 | 14.49 ± 2.63 | 6.26 ± 0.67 | 0.47 ± 0.35 |
| 3 | 10.64 ± 1.19 | 8.08 ± 0.70 | 1.53 ± 1.08 | 15.23 ± 2.41 | 6.44 ± 0.60 | 0.40 ± 0.08 |
| 4 | 9.56 ± 0.79 | 6.24 ± 0.40 | 0.24 ± 0.28 | 12.93 ± 2.10 | 5.58 ± 0.33 | -0.13 ± 0.90 |
| 5 | 10.35 ± 0.73 | 6.53 ± 0.23 | 1.17 ± 1.31 | 13.30 ± 2.14 | 5.18 ± 0.15 | -0.07 ± 0.93 |

The elution results of the collagen films in water and saline are shown in Table 4. For silver, the highest elution rate was on day 1 (19.08±0.92 ppm in water, 20.34±1.42 ppm in saline). Then the elution rate decreased, but the elution rate was still higher than 10 ppm in water, and 13 ppm in saline. There was more silver eluted out in saline than in water. In total 54.03% and 66.22% silver were eluted out from collagen films in water and in saline respectively over the 5 days. For zinc the highest elution rate in water was on day 1 (9.86±0.39 ppm). Then the elution rate slightly decreased, but kept above 6.5 ppm at day 5. However, the elution rate in saline remained constant at around 6 ppm from day 1 to day 5. Overall, 37.89% and 27.36% zinc was eluted out from collagen films in water and in saline respectively for 5 days. For EDTA, the results show that most EDTA eluted out in day 1 both in water and in saline. After day 1, only a small amount EDTA was eluted out. In total, there was 16.95% and 13.44% EDTA eluted out from collagen films in water and in saline respectively over 5 days.

Gauze Platform and Elution of EDTA Compound 4

Pieces of gauze was soaked in water, 2% EDTA, 4% EDTA and either EDTA compound 4 in high concentration (sample 1) or in low concentration (sample 2) for 1 hour; then the gauze was taken out and put into a 60 mm polystyrene culture plate and dried in fume hood for 24 hours. The gauzes were weighed before soaking, after soaking and after drying for 24 hours.

TABLE 5

The percentage of weight change after soaking in different solutions

| | Water | 2% EDTA | 4% EDTA | EDTA compound 4, sample 1 (EDTA-Ag—Zn) | EDTA compound 4, sample 2 (EDTA-Ag—Zn) |
|---|---|---|---|---|---|
| Weight variety (%) | 0.133 | 28.12 | 56.87 | 47.03 | 47.55 |
| STDEV | 0.07 | 0.71 | 2.13 | 3.74 | 1.66 |

To assess the elution profile of the EDTA complexes from gauze, the loaded gauzes were immersed in water and saline (Table 6 and Table 7). The results showed that silver, zinc and EDTA eluted out rapidly at day 1 and day 2 in both water and saline. After day 2, the eluting of silver, zinc and EDTA decreased more than 5 times compared to day 1.

TABLE 6

Elution profile of EDTA compound 4, sample 1 from loaded gauze in water and saline

| Time | Elution in water (ppm) | | | Elution in saline (ppm) | | |
|---|---|---|---|---|---|---|
| (days) | Silver | Zinc | EDTA | Silver | Zinc | EDTA |
| 1 | 35.89 ± 5.66 | 21.99 ± 2.85 | 18.09 ± 3.19 | 49.91 ± 2.29 | 29.69 ± 2.40 | 24.65 ± 2.40 |
| 2 | 25.27 ± 5.63 | 15.66 ± 2.73 | 12.54 ± 3.11 | 12.76 ± 4.44 | 9.14 ± 2.77 | 9.19 ± 3.42 |
| 3 | 4.93 ± 2.56 | 4.42 ± 1.62 | 1.90 ± 0.79 | 3.43 ± 0.54 | 3.71 ± 0.27 | 1.83 ± 0.26 |
| 4 | 1.75 ± 0.76 | 3.26 ± 0.35 | 1.27 ± 0.84 | 2.29 ± 1.73 | 3.42 ± 0.93 | 1.28 ± 0.84 |
| 5 | 0.85 ± 0.34 | 2.06 ± 1.21 | 0.87 ± 0.36 | 2.52 ± 2.26 | 2.68 ± 2.00 | 0.45 ± 0.15 |

TABLE 7

Elution profile of EDTA compound 4, sample 2 from loaded gauze in water and saline

| Time | Elution in water (ppm) | | | Elution in saline (ppm) | | |
|---|---|---|---|---|---|---|
| (days) | Silver | Zinc | EDTA | Silver | Zinc | EDTA |
| 1 | 23.32 ± 3.95 | 17.08 ± 3.09 | 13.23 ± 1.28 | 27.32 ± 3.84 | 22.71 ± 1.75 | 17.31 ± 1.77 |
| 2 | 16.28 ± 3.75 | 12.78 ± 1.55 | 8.74 ± 2.01 | 8.36 ± 2.37 | 7.67 ± 2.03 | 6.84 ± 2.67 |
| 3 | 3.82 ± 1.39 | 4.21 ± 1.19 | 1.55 ± 0.56 | 2.55 ± 0.94 | 3.70 ± 0.20 | 1.75 ± 0.31 |
| 4 | 1.42 ± 0.40 | 3.37 ± 0.26 | 1.13 ± 0.57 | 1.46 ± 0.99 | 3.48 ± 0.68 | 1.11 ± 0.61 |
| 5 | 0.59 ± 0.35 | 2.49 ± 0.88 | 0.79 ± 0.19 | 1.57 ± 1.43 | 2.95 ± 1.46 | 0.54 ± 0.11 |

Incorporation of EDTA Complexes into Hydrogels

Hydrogels were loaded with EDTA compounds and investigated for elution of the silver, zinc and EDTA. Carbopol ETD 2020 was obtained from Lubrizol Advanced Materials, Inc. USA. 1.2 g carbopol power was dissolved in 42.36 g deionized water for 1 hour to fully hydrate. Then 8.4 ml of the EDTA complexes and 4.8 g glycerine were added into carbopol solution with vigorous stirring; finally, 3 g 50% triethanolamine was dropped into the suspension to obtain final products: carbopol hydrogel with EDTA complexes.

The cumulative elution profiles of the EDTA complexes from the hydrogels into water and saline are shown in Table 8 and Table 9. The results show that silver, zinc and EDTA eluted out rapidly in day 1 and there was no distinct cumulative eluting after day 1 in water. The silver, zinc and EDTA increased in saline day by day, which indicated the release of silver, zinc and EDTA can be controlled from the hydrogel.

TABLE 8

Cumulative Elution profile of EDTA compound 4, sample 1 loaded onto hydrogel into water and saline

| Time | Elution in water (ppm) | | | Elution in saline (ppm) | | |
|---|---|---|---|---|---|---|
| (days) | Silver | Zinc | EDTA | Silver | Zinc | EDTA |
| 1 | 44.39 ± 5.98 | 31.88 ± 3.53 | 31.12 ± 5.40 | 32.09 ± 3.02 | 22.12 ± 3.31 | 26.39 ± 2.06 |
| 2 | 47.13 ± 5.03 | 36.09 ± 3.61 | 26.21 ± 4.20 | 37.09 ± 2.91 | 30.90 ± 5.81 | 27.18 ± 2.34 |
| 3 | 45.58 ± 4.54 | 34.28 ± 4.55 | 37.28 ± 2.58 | 47.05 ± 2.79 | 36.73 ± 3.64 | 35.02 ± 0.72 |
| 4 | 46.88 ± 6.86 | 33.78 ± 2.20 | 37.53 ± 3.27 | 51.24 ± 1.53 | 40.31 ± 1.84 | 37.71 ± 1.92 |
| 5 | 45.91 ± 7.04 | 35.99 ± 1.16 | 35.11 ± 5.39 | 59.55 ± 1.21 | 43.22 ± 3.91 | 40.57 ± 1.41 |

TABLE 9

Cumulative Elution profile of EDTA compound 4, sample 2 loaded onto hydrogel in water and saline

| Time | Elution in water (ppm) | | | Elution in saline (ppm) | | |
|---|---|---|---|---|---|---|
| (days) | Silver | Zinc | EDTA | Silver | Zinc | EDTA |
| 1 | 28.41 ± 3.48 | 20.77 ± 3.25 | 20.80 ± 3.07 | 21.10 ± 1.80 | 15.30 ± 2.12 | 16.64 ± 1.41 |
| 2 | 29.03 ± 4.71 | 23.57 ± 2.12 | 22.50 ± 2.86 | 26.06 ± 2.03 | 20.51 ± 3.94 | 17.31 ± 1.43 |
| 3 | 29.12 ± 2.73 | 22.53 ± 7.30 | 24.64 ± 1.57 | 31.27 ± 0.96 | 23.98 ± 1.92 | 21.81 ± 0.42 |
| 4 | 29.89 ± 3.51 | 22.23 ± 1.97 | 24.30 ± 1.51 | 32.50 ± 0.96 | 26.11 ± 1.08 | 22.70 ± 1.70 |
| 5 | 30.64 ± 5.25 | 23.54 ± 1.23 | 23.03 ± 3.46 | 37.54 ± 0.61 | 27.28 ± 3.01 | 25.02 ± 0.96 |

Silver Content 1 g hydrogel was placed in 10 ml 37% nitric acid to dissolve. After filtration, the solution was diluted to an exact volume of 0.5 ml. The diluted solutions were mixed with 0.5 ml 1% sodium dodecyl sulphate (SDS) and 0.5 ml of 1 M sulphuric acid followed by the addition of 0.5 ml $1 \times 10^{-3}$ M dithizone solution. The absorbance was measured at 490 nm against a corresponding reagent blank. The silver content in an unknown sample was determined using a concurrently prepared calibration graph. The concentration of silver was then measured against series of calibration standards by modified spectrophotometry. Concentration is then converted to a weight % based on the weight of dressing used.

The results of the silver content experiments on the hydrogel measured by spectrophotometry are shown in the Table 10. The results show that the low level silver hydrogel had 0.095% silver only, there was 0.101% silver (w/w) in the EDTA compound 4, sample 1 (high levels of EDTA-Ag—Zn) hydrogel and 0.046% silver (w/w) in the other EDTA compound 4, sample 1 hydrogel (low levels of EDTA-Ag—Zn).

TABLE 10

The silver content in the hydrogels (%)

| Control Hydrogel | Silver Hydrogel | EDTA compound 4, sample 2 (low) | EDTA compound 4, sample 1 (high) |
|---|---|---|---|
| 0 | 0.095 ± 0.006 | 0.046 ± 0.008 | 0.101 ± 0.021 |

Water Donation/Absorption

Table 11 shows that all the hydrogels belong to 1 b or 1c type. That means all the hydrogels are donation type. The tetra sodium EDTA only hydrogel was found to be in the 1c hydrogel group (donated the most fluid); other gels were characterised as 1 b gels, which donated 5 to 10% water from hydrogel to gelatin.

TABLE 11

Water donation/absorption results

| Hydrogel | Mean % increase in hydrogel weight (Agar as test gel) | Mean % decrease in hydrogel weight (Gelatin as test gel) | Gel type |
|---|---|---|---|
| Control Hydrogel | −3.17 ± 0.83 | 9.85 ± 0.44 | 1b |
| Silver Hydrogel (0.1%) | 2.10 ± 0.14 | 8.81 ± 0.56 | 1b |
| Zinc Hydrogel (0.06%) | 0.18 ± 0.13 | 7.97 ± 1.33 | 1b |
| Tetrasodium EDTA Hydrogel (0.2%) | −2.99 ± 1.22 | 10.16 ± 2.71 | 1c |
| EDTA compound 4, sample 2 Hydrogel (EDTA-Zn—Ag - low - 0.05% silver) | 1.56 ± 0.29 | 5.33 ± 0.94 | 1b |
| EDTA compound 4, sample 1 Hydrogel (EDTA-Zn—Ag - high - 0.1% silver) | 2.43 ± 0.47 | 5.29 ± 0.40 | 1b |

Microbiological Analysis of the EDTA Complexes

Microbiological Evaluation of Tetra Sodium EDTA

Initial testing on tetrasodium EDTA showed tetrasodium EDTA was ineffective as a treatment against immature and mature *S. aureus* and *P. aeruginosa* biofilms at short contract times (Table 12, Table 13 and Table 14). The incorporation of tetrasodium EDTA into fibrous dressing frameworks did however result in a 3-Log reduction, respectively, in *S. aureus* and *P. aeruginosa* biofilm following 24 hours of treatment (Table 15 and Table 15).

TABLE 12

Efficacy of tetrasodium EDTA against *P. aeruginosa* and *S. aureus* 24-hour biofilm

| | MIC | | | | MBC | | | | MBEC | | | |
|---|---|---|---|---|---|---|---|---|---|---|---|---|
| | 1 min | 30 min | 1 h | 24 h | 1 min | 30 min | 1 h | 24 h | 1 min | 30 min | 1 h | 24 h |
| *P. aeruginosa* | 25 | 12.5 | 25 | 6.25 | 50 | 50 | 25 | 6.25 | x | x | 6.25 | 6.25 |
| *S. aureus* | 25 | 12.5 | 25 | 6.25 | 50 | 50 | 25 | 6.25 | x | x | 6.25 | 6.25 |

Minimum inhibitory concentration (MIC), minimum biocidal concentration (MBC) and minimum biofilm eradication (MBEC) were determined. Values represent a percentage of the stock antimicrobial solution (8%). The 'x' denotes that all concentrations of the antimicrobial tested, including the antimicrobial in neat form, were ineffective.

TABLE 13

Log reduction (LR) and percentage kill (%) values of *S. aureus* biofilms when exposed to tetra sodium EDTA

| | *S. aureus* | | | | | | | | | | | |
|---|---|---|---|---|---|---|---|---|---|---|---|---|
| | 24-Hour Biofilms | | | | | | 72-Hour Biofilms | | | | | |
| | Treatment Time | | | | | | | | | | | |
| | 1 | | 5 | | 15 | | 1 | | 5 | | 15 | |
| Antimicrobial | | | | | | | | | | | | |
| | LR | Kill (%) | LR | Kill (%) | LR | Kill (%) | LR | Kill (%) | LR | Kill (%) | LR | Kill (%) |
| Tetrasodium EDTA (4%) | 1.59 ± 1.56 | 97.41 | 0.40 ± 0.05 | 59.90 | 0.71 ± 0.11 | 80.51 | 0.34 ± 0.37 | 54.09 | 0.70 ± 0.05 | 79.86 | 0.70 ± 0.02 | 80.25 |
| Untreated control | Mean Log$_{10}$ density of 6.93 ± 0.05<br>LR - 0<br>Kill (%) - 0 | | | | | | Mean Log$_{10}$ density of 7.58 ± 0.05<br>LR - 0<br>Kill (%) - 0 | | | | | |

Mean Log values were calculated and the standard error (SE) of the mean LR was determined (LR±SE). The Mean Log$_{10}$ density of untreated controls was calculated (±standard deviation).

TABLE 14

Log reduction (LR) and percentage kill (%) values of *P. aeruginosa* biofilms when exposed to tetra sodium EDTA at varying concentrations.

| | *P. aeruginosa* | | | | | | | | | | | |
|---|---|---|---|---|---|---|---|---|---|---|---|---|
| | 24-Hour Biofilms | | | | | | 72-Hour Biofilms | | | | | |
| | Treatment Time | | | | | | | | | | | |
| | 1 | | 5 | | 15 | | 1 | | 5 | | 15 | |
| Antimicrobial | | | | | | | | | | | | |
| | LR | Kill (%) | LR | Kill (%) | LR | Kill (%) | LR | Kill (%) | LR | Kill (%) | LR | Kill (%) |
| Tetrasodium EDTA (4%) | 0.77 ± 0.08 | 83.018 | 1.68 ± 0.05 | 97.92 | 2.31 ± 0.10 | 99.51 | 2.10 ± 0.05 | 99.22 | 2.35 ± 0.02 | 99.56 | 1.31 ± 0.12 | 95.07 |
| Untreated control | Mean Log$_{10}$ density of 7.62 ± 0.03<br>LR - 0<br>Kill (%) - 0 | | | | | | Mean Log$_{10}$ density of 7.83 ± 0.15<br>LR - 0<br>Kill (%) - 0 | | | | | |

Mean Log values were calculated and the standard error (SE) of the mean LR was determined (LR±SE). The Mean Log$_{10}$ density of untreated controls was calculated (±standard deviation).

TABLE 15

The antimicrobial activity of tetra sodium EDTA (at varying concentrations) - incorporated fibrous dressing against *S. aureus* using the direct contact method

| Dressing | Time 24 Log$_{10}$ Density ± SD | Time 24 Log$_{10}$ Reduction | Microbicidal/ Microbistatic |
|---|---|---|---|
| Untreated fibrous dressing (Negative control) | 8.88 ± 0.05 | 0 | Microbistatic |
| Durafiber | 8.85 ± 0.15 | 0.90 | Microbistatic |
| AQUACEL Ag (Positive control) | 2.88 ± 0 | 6.88 | Microbicidal |
| Fibrous Dressing 1 | 6.35 ± 0.26 | 3.40 | Microbicidal |
| Fibrous Dressing 2 | 6.28 ± 0.05 | 3.47 | Microbicidal |
| Fibrous Dressing 3 | 6.31 ± 0.03 | 3.44 | Microbicidal |
| Fibrous Dressing 4 | 8.74 ± 0.07 | 1.01 | Microbistatic |
| Fibrous Dressing 5 | 8.80 ± 0.07 | 0.95 | Microbistatic |
| Fibrous Dressing 6 | 9.02 ± 0.02 | 0.73 | Microbistatic |

Results for the antimicrobial effectiveness of the dressing were expressed as microbicidal ($Log_{10}$ Reduction ≥3) or microbistatic ($Log_{10}$ Reduction ≤3). SD represents standard deviation. Experiment was performed on triplicate dressings.

TABLE 16

The antimicrobial activity of EDTA-incorporated fibrous dressing against *P. aeruginosa* using the direct contact method

| Dressing | Time 24 $Log_{10}$ Density ± SD | Time 24 $Log_{10}$ Reduction | Microbicidal/ Microbistatic |
|---|---|---|---|
| Untreated chitosan (Negative control) | 9.75 ± 0.59 | 0 | Microbistatic |
| Durafiber | 9.57 ± 0.53 | 0.18 | Microbistatic |
| AQUACEL Ag (Positive control) | 2.30 ± 0.35 | 7.45 | Microbicidal |
| Fibrous Dressing 1 | 6.41 ± 0.95 | 3.34 | Microbicidal |
| Fibrous Dressing 2 | 6.45 ± 1.01 | 3.31 | Microbicidal |
| Fibrous Dressing 3 | 9.21 ± 0.07 | 0.54 | Microbistatic |
| Fibrous Dressing 4 | 9.46 ± 0.11 | 0.29 | Microbistatic |
| Fibrous Dressing 5 | 9.80 ± 0.03 | −0.05 | Microbistatic |
| Fibrous Dressing 6 | 9.63 ± 0.07 | 0.12 | Microbistatic |

Results for the antimicrobial effectiveness of the dressing were expressed as microbicidal ($Log_{10}$ Reduction ≥3) or microbistatic ($Log_{10}$ Reduction ≤3). SD represents standard deviation. Experiment was performed on triplicate dressings.

Microbiological Evaluation of EDTA Complexes (EDTA-Ag—Zn and EDTA-Ag—Cu)

Different EDTA complexes achieved complete kill in *S. aureus* and *P. aeruginosa* biofilms (Table 17).

TABLE 17

Number of colonies detected following exposure of 24-hour CDC biofilms to different EDTA compounds: EDTA-Cu, EDTA-$Ag_2$—Cu (compound 2), EDTA-$Ag_2$—Zn (compound 4), EDTA-Ag—Zn—Na (compound 3).

| | Compound | | | |
|---|---|---|---|---|
| Microorganism | Cu—Na-EDTA Cfu/ml | $Ag_2$—Cu-EDTA Cfu/ml | $Ag_2$—Zn-EDTA Cfu/ml | Ag—Zn—Na-EDTA Cfu/ml |
| *S. aureus* | 0 | 0 | 0 | 0 |
| *P. aeruginosa* | 0 | 0 | 0 | 0 |

EDTA compounds 1-4 (prepared as described above) were tested against *P. aeruginosa* and *S. aureus* biofilms at a concentration of 100 ppm silver, to which the compounds Ag/Cu/NaEDTA and Ag/Zn/NaEDTA showed 100% kill in *S. aureus* and at a 3.5 log reduction in *P. aeruginosa* (Table 18).

TABLE 18

Log reduction (LR) and percentage kill (%) values of *S. aureus* and *P. aeruginosa*.

| | *P. aeruginosa* | | *S. aureus* | |
|---|---|---|---|---|
| EDTA compound | LR | Kill (%) | LR | Kill (%) |
| 1 | 3.88 ± 0.15 | 99.99 | N.D | 100 |
| 3 | 3.51 ± 0.04 | 99.97 | N.D | 100 |
| 2 | 3.31 ± 0.01 | 99.95 | 4.0 ± 0.20 | 99.99 |
| 4 | 3.34 ± 0.11 | 99.95 | 3.73 ± 0.18 | 99.98 |
| Untreated control | 0 ± 0.07 | 0 | 0 ± 0.01 | 0 |

Microbial cultures were exposed to compounds for 24 hours. Compounds were diluted according to 100 ppm of silver. Biofilms were formed using the CDC bioreactor. Samples were performed in triplicate. Mean Log values were calculated and the standard error (SE) of the mean LR was determined (LR±SE). Given that the log of zero is mathematically undefined, in cases whereby no colonies were detected following antimicrobial treatment, 'N.D' for 'not determined' is used.

The anti-biofilm efficacy of the EDTA-Ag—Zn compound as a liquid was evaluated using the MBEC model. 100% kill of *P. aeruginosa* biofilms (no viable colonies detected) following treatment with various concentrations of the complexes (1000 ppm-62.5 ppm) was observed (Table 19).

TABLE 19

Log reduction values related to the treatment of *S. aureus* and *P. aeruginosa* 48-hour biofilms with EDTA-$Ag_2$—Zn compound (EDTA compound 4)

| | Treatment time | | | |
|---|---|---|---|---|
| | 1 hours | | 24 hours | |
| Treatment | LR | % Kill | LR | % Kill |
| 1000 ppm | N.D | 100 | N.D | 100 |
| 500 ppm | N.D | 100 | N.D | 100 |
| 250 ppm | N.D | 100 | N.D | 100 |
| 125 ppm | N.D | 100 | N.D | 100 |
| 62.5 ppm | N.D | 100 | N.D | 100 |
| *P. aeruginosa* control (Mean Log density) | 6.19 ± 0.05 | | 6.85 ± 0.15 | |

Biofilms were formed using the MBEC plate method. Log reduction (LR) values are expressed with standard error. N.D (not determined) is stated when no colonies were detected upon enumeration.

Anti-Biofilm Ability (MBEC)

The MBEC model (ASTM E2799) was used to assess the anti-biofilm efficacy of the liquid formulas. Biofilms were grown on polystyrene pegs in the MBEC model for either 24 or 48 hours before treatment. Using the liquid form of the EDTA complexes 24- and 48-hour biofilms were tested (Table 20). The results show that the complexes and silver solution (50 ppm and 100 ppm) caused 100% kill of 24- and 48-hour biofilms. Similarly, 4% tetrasodium EDTA caused 100% kill in 24 and 48 hours on *S. aureus*, MRSA, *S. epidermidis* and *E. faecalis* biofilms. However for *P. aeruginosa* 24- and 48-hour biofilms there was a 5.94±3.43 and 6.99±4.04 log reduction respectively. The increase in log reduction for 48-hour biofilms when compared with 24-hour biofilms highlights the efficacy of the EDTA complexes as an anti-biofilm agent.

TABLE 20

MBEC results for tetrasodium EDTA and EDTA compound 4.

| Treatment | 24-Hour Biofilm | | 48-Hour Biofilm | |
|---|---|---|---|---|
| | LR | Kill % | LR | Kill % |
| S. aureus ATCC 29213 Control | 0 ± 0 | 0 | 0 ± 0 | 0 |
| tEDTA (4%) | 6.44 | 100 | 6.50 | 100 |
| Silver 100 ppm | 6.44 | 100 | 6.50 | 100 |
| Silver 50 ppm | 6.44 | 100 | 6.50 | 100 |
| EDTA-Ag$_2$—Zn (compound 4) 100 ppm | 6.44 | 100 | 6.50 | 100 |
| EDTA-Ag$_2$—Zn (compound 4) 50 ppm | 6.44 | 100 | 6.50 | 100 |
| S. aureus MRSA BAA-43 control | 0 ± 0 | 0 | 0 ± 0 | 0 |
| tEDTA (4%) | 5.40 | 100 | 6.43 | 100 |
| Silver 100 ppm | 5.40 | 100 | 6.43 | 100 |
| Silver 50 ppm | 5.40 | 100 | 6.43 | 100 |
| EDTA-Ag$_2$—Zn (compound 4) 100 ppm | 5.40 | 100 | 6.43 | 100 |
| EDTA-Ag$_2$—Zn (compound 4) 50 ppm | 5.40 | 100 | 6.43 | 100 |
| P. aeruginosa NCTC 10662 control | 0 ± 0 | 0 | 0 ± 0.03 | 0 |
| tEDTA (4%) | 5.94 ± 3.43 | 99.9998 | 6.99 ± 4.04 | 99.9999 |
| Silver 100 ppm | 7.44 | 100 | 8.44 | 100 |
| Silver 50 ppm | 7.44 | 100 | 8.44 | 100 |
| EDTA-Ag$_2$—Zn (compound 4) 100 ppm | 7.44 | 100 | 8.44 | 100 |
| EDTA-Ag$_2$—Zn (compound 4) 50 ppm | 7.44 | 100 | 8.44 | 100 |
| S. epidermidis ATCC 35984 | 0 ± 0 | 0 | 0 ± 0 | 0 |
| tEDTA (4%) | 6.09 | 100 | 6.41 | 100 |
| Silver 100 ppm | 6.09 | 100 | 6.41 | 100 |
| Silver 50 ppm | 6.09 | 100 | 6.41 | 100 |
| EDTA-Ag$_2$—Zn (compound 4) 100 ppm | 6.09 | 100 | 6.41 | 100 |
| EDTA-Ag$_2$—Zn (compound 4) 50 ppm | 6.09 | 100 | 6.41 | 100 |
| E. faecalis ATCC 29212 | 0 ± 0 | 0 | 0 ± 0 | 0 |
| tEDTA (4%) | 6.35 | 100 | 6.40 | 100 |
| Silver 100 ppm | 6.35 | 100 | 6.40 | 100 |
| Silver 50 ppm | 6.35 | 100 | 6.40 | 100 |
| EDTA-Ag$_2$—Zn (compound 4) 100 ppm | 6.35 | 100 | 6.40 | 100 |
| EDTA-Ag$_2$—Zn (compound 4) 50 ppm | 6.35 | 100 | 6.40 | 100 |

24- and 48-hour biofilms were formed using MBEC plate method and treated for 24 hours. Technical replicates n=3. Log reduction (LR) values show±standard error (SE) of LR value. The Log densities±standard deviation for untreated controls (24-hour and 48-hour biofilms) are: P. aeruginosa NCTC 10662 (7.44±0.06 and 8.44±0.034), S. aureus ATCC 29213 (6.45±0.05 and 6.50±0.38), S. aureus MRSA BAA-43 (5.40±0.41 and 6.43±0.25), E. faecalis ATCC 29212 (6.35±0.04 and 6.40±0.09) and S. epidermidis ATCC 35984 (6.09±0.36 and 6.41±0.62).

Impregnation of Gauze with the Complexes

Gauze impregnated with the EDTA-Ag$_2$—Zn compound 4 showed complete biofilm kill after 24 hours (see Table 21), which correlated with elution data whereby the largest amount of silver and EDTA eluted at 24 hours. Furthermore, gauze containing the EDTA-Ag$_2$—Zn compound 4 was more effective than tetrasodium EDTA at 2% and 4%. There was a greater log reduction in biofilms when treated with gauze containing 4% EDTA than 2% EDTA. The collagen film containing the compound was less effective than the gauze.

TABLE 21

Log reduction (LR) and percentage kill (%) values of S. aureus and P. aeruginosa biofilms following treatment in the filter model.

| | P. aeruginosa | | S. aureus | |
|---|---|---|---|---|
| Treatment | LR | Kill (%) | LR | Kill (%) |
| Control gauze | 1.84 ± 1.06 | 98.55 | 0.42 ± 0.24 | 61.75 |
| Gauze 2% tEDTA | 2.05 ± 1.18 | 99.11 | 0.56 ± 0.32 | 72.43 |
| Gauze 4% tEDTA | 3.40 ± 1.96 | 99.96 | 1.22 ± 0.70 | 93.98 |
| Gauze + EDTA-Ag—Zn compound | N.D | 100 | N.D | 100 |
| Collagen film + EDTA-Ag$_2$—Zn (compound 4) | 2.85 ± 1.64 | 99.86 | 4.04 ± 2.33 | 99.991 |
| Untreated control | Mean log density: 10.20 | | Mean log density: 9.88 | |

Biofilms (48-hours) were exposed to various platforms for 24 hours. The compound used to impregnate the platforms was EDTA-Ag$_2$—Zn (compound 4). Samples were run in triplicate. Mean Log values were calculated and the standard error (SE) of the mean LR was determined (LR±SE). In cases whereby no colonies were detected following treatment, 'N.D' for 'not determined' is used, which represents 100% kill. Table 21 provides evidence that the complexes of the present invention demonstrate potential synergy between agents and out performed tetra sodium EDTA.

Addition of the Complexes to a Hydrogel

The CDC biofilm bioreactor model (ASTM E2871) was used to test anti-biofilm efficacy of the hydrogel formulations. Biofilms were grown on polycarbonate coupons in the bioreactor for 48 hours (48-hour) biofilm. The formulation of a hydrogel containing the complexes showed complete biofilm kill in the CDC model after 24 hours of treatment (see Table 22). The hydrogel containing the compound 4 outperformed the hydrogel containing silver alone.

TABLE 22

Log reduction (LR) and percentage kill (%) values of S. aureus and
P. aeruginosa biofilms following treatment in the CDC model.

| | P. aeruginosa | | S. aureus | |
|---|---|---|---|---|
| Treatment | LR | Kill (%) | LR | Kill (%) |
| Control hydrogel | 1.38 ± 0.80 | 95.81 | 0 | 0 |
| Hydrogel + silver | 5.13 ± 2.96 | 99.9992 | 0 | 0 |
| Hydrogel + compound 4 | N.D | 100 | ND | 100 |
| Untreated control | Mean log density: 8.97 | | Mean log density: 4.70 | |

Biofilms (48-hours) were exposed to hydrogel for 24 hours. The compound used to impregnate the platforms was EDTA-Ag$_2$—Zn (compound 4). Samples were run in triplicate. Mean Log values were calculated and the standard error (SE) of the mean LR was determined (LR±SE). In cases whereby no colonies were detected following treatment, 'N.D' for 'not determined' is used, which represents 100% kill. Table 22 demonstrates evidence that the complex of EDTA-Ag$_2$—Zn outperformed a silver hydrogel alone in antibiofilm activity.

To test the anti-biofilm efficacy of the hydrogel EDTA-Ag$_2$—Zn compound 4, we tested the hydrogel against five microorganisms in biofilm form using the CDC biofilm bioreactor. The hydrogel control showed a slight log reduction in microbial numbers. Hydrogel containing silver resulted in 100% kill in S. aureus, MRSA, S. epidermidis and E. faecalis. However the silver hydrogel only caused a 3.16±1.83 log reduction in P. aeruginosa (Table 23). The hydrogel containing zinc caused between a 1.24 to 1.84 log reduction respectively in all microorganisms except for S. epidermidis, whereby 100% kill was recorded. Similarly, hydrogel containing tetrasodium EDTA caused a slight log reduction in most microorganisms, however caused a 100% kill in S. epidermidis. The hydrogel formulation containing a low concentration of the compound 4 (EDTA-Ag$_2$—Zn) did not have a significant reduction in most microorganisms but did cause a 100% kill in S. epidermidis. The high concentration of the compound 4 incorporated into the hydrogel caused 100% kill in all microbial biofilms tested.

TABLE 23

Log reduction (LR) and percentage kill (%) values of 48-hour biofilms
following treatment with hydrogel formulations in the CDC model. Biofilms (48-hours)
were exposed to hydrogel for 24 hours at 37° C. ± 2° C. The compound used to impregnate the
platforms was EDTA-Ag$_2$—Zn (compound 4) at a low and high concentration. Samples were run
in triplicate. Mean Log values were calculated and the standard error (SE) of the mean LR
was determined (LR ± SE). The mean log density (mean log density ± standard deviation) of
each microorganism is stated.

| | P. aeruginosa | | S. aureus | | MRSA | | S. epidermidis | | E. faecalis | |
|---|---|---|---|---|---|---|---|---|---|---|
| Treatment | LR | Kill (%) | LR | Kill (%) | LR | Kill (%) | LR | Kill (%) | LR | Kill (%) |
| Untreated control | 0 ± 0 | 0 | 0 ± 0 | 0 | 0 ± 0 | 0 | 0 ± 0 | 0 | 0 ± 0 | 0 |
| Control hydrogel | 1.15 ± 0.66 | 92.89 | 0.79 ± 0.45 | 83.62 | 0.82 ± 0.47 | 84.92 | 0.20 ± 0.12 | 37.40 | 0.44 ± 0.25 | 63.67 |
| Hydrogel + silver (0.1%) | 3.16 ± 1.83 | 99.93 | 5.47 | 100 | 5.71 | 100 | 5.54 | 100 | 5.99 | 100 |
| Hydrogel + zinc (0.06%) | 1.49 ± 0.84 | 96.53 | 1.84 ± 1.06 | 98.56 | 1.80 ± 1.04 | 98.43 | 5.54 | 100 | 1.24 ± 0.72 | 94.24 |
| Hydrogel + tEDTA (0.2%) | 1.66 ± 0.96 | 97.80 | 1.64 ± 0.95 | 97.71 | 1.38 ± 0.79 | 95.78 | 5.54 | 100 | 1.68 ± 0.97 | 97.90 |
| Hydrogel + compound 4 EDTA-Ag—Zn (low - 0.05% silver) | 1.58 ± 0.91 | 97.36 | 1.46 ± 0.85 | 96.56 | 1.50 ± 0.86 | 96.81 | 5.54 | 100 | 1.52 ± 0.88 | 97.00 |
| Hydrogel + complex - EDTA-Ag—Zn (high - 0.1% silver) | 7.53 | 100 | 5.47 | 100 | 5.71 | 100 | 5.54 | 100 | 5.99 | 100 |
| Hydrogel control | Mean log density: 7.53 ± 0.06 | | Mean log density: 5.47 ± 0.05 | | Mean log density: 5.71 ± 0.05 | | Mean log density: 5.54 ± 0.11 | | Mean log density: 5.99 ± 0.17 | |

Table 23 demonstrates that the compound 4 (EDTA-Ag$_2$—Zn) outperformed a silver hydrogel alone, a zinc hydrogel alone and to tetra sodium EDTA alone, in antibiofilm activity.

Cellular Data

Direct cytotoxicity was tested using the Neutral Red Uptake assay, whereby uptake of Neutral Red by cells is proportional to the cell viability (Borenfreund, E. & Puerner, J. A. 1985, A simple quantitative procedure using monolayer cultures for cytotoxicity assays (HTD/NR-90), *Methods in Cell Science*, 9, 7-9). According to the international standard ISO 10993-5 (Wallin, R. F. & Arscott, E. 1998, A practical guide to ISO 10993-5: Cytotoxicity. *Medical Device and Diagnostic Industry*, 20, 96-98), if the percentage viability is less than 70% of the untreated control, then the substance is considered cytotoxic. Results showed that increasing concentrations of tetrasodium EDTA were cytotoxic to cells with percentage viability between 3.87% and 14.23%. All concentrations of Compounds 1 and 3 were classed as cytotoxic, with viability ranging from 52.57% to 53.66% and 46.46% to 63.08%, respectively. Compound 2 at all concentrations was interpreted as non-cytotoxic with percentage viability ranging from 72.01% and 72.21%. Compound 4 at 50 ppm was also non-cytotoxic, will 72.93% viability, however other concentrations were cytotoxic (Table 24). The agar diffusion method for indirect cytotoxicity allows for the qualitative assessment of cytotoxicity. According to ISO 10993-5, an achievement of a numerical grade greater than 2 is considered a cytotoxic effect.

TABLE 24

Percentage cell viability using the direct contact method. Direct cytotoxicity was performed using Neutral Red on EDTA compounds 1-4. Viability was expressed as the percentage of control ± standard deviation. Samples were tested in triplicate.

| Sample | Percentage of Control/ Percentage Viability (%) | Interpretation |
| --- | --- | --- |
| DMEM (Negative control) | 100 ± 0 | Non cytotoxic |
| SDS 0.2 mg/ml | 6.57 ± 0 | Cytotoxic |
| SDS 0.15 mg/ml | 6.57 ± 0 | Cytotoxic |
| SDS 0.1 mg/ml | 6.57 ± 0 | Cytotoxic |
| SDS 0.05 mg/ml | 6.57 ± 0 | Cytotoxic |
| EDTA 2% | 3.87 ± 0.66 | Cytotoxic |
| EDTA 4% | 4.79 ± 1.74 | Cytotoxic |
| EDTA 8% | 7.03 ± 1.21 | Cytotoxic |
| EDTA 10% | 10.22 ± 7.23 | Cytotoxic |
| EDTA 15% | 14.23 ± 13.02 | Cytotoxic |
| Compound 1 100 ppm | 52.57 ± 8.97 | Cytotoxic |
| Compound 1 50 ppm | 53.66 ± 9.48 | Cytotoxic |
| Compound 1 25 ppm | 51.54 ± 9.44 | Cytotoxic |
| Compound 3 100 ppm | 46.46 ± 2.40 | Cytotoxic |
| Compound 3 50 ppm | 63.08 ± 8.47 | Cytotoxic |
| Compound 3 25 ppm | 50.20 ± 17.08 | Cytotoxic |
| Compound 2 100 ppm | 72.09 ± 17.57 | Non cytotoxic |
| Compound 2 50 ppm | 72.01 ± 7.41 | Non cytotoxic |
| Compound 2 25 ppm | 72.21 ± 3.74 | Non cytotoxic |
| Compound 4 100 ppm | 56.41 ± 1.83 | Cytotoxic |
| Compound 4 50 ppm | 72.93 ± 12.90 | Non cytotoxic |
| Compound 4 25 ppm | 62.67 ± 20.39 | Cytotoxic |

Table 24 demonstrates that the compounds of the present invention were significantly lower in toxicity when compared to tetra sodium EDTA alone.

The assessment of the Zone Index for EDTA at all concentrations showed cytotoxicity, with zones of no neutral red uptake extended 0.5 cm to 1 cm beyond the filter disc. Despite this finding, the Lysis Index interpretation showed that EDTA at 2%, 4% and 8% was not cytotoxic to cells, whereas 10% and 15% concentrations were cytotoxic. Compound 1 at 100 ppm and 50 ppm was interpreted as cytotoxic to cells according to the zone index, whereby the zone of cells showing no neutral red uptake extended 0.5 cm to 1 cm beyond the filter disc specimen. However these concentrations were not deemed cytotoxic when interpreting the Lysis Index. Compound 1 at 25 ppm was not cytotoxic to cells. Compound 3 at 100 ppm resulted in cell cytotoxicity according to the Zone Index but not the Lysis Index. Compounds 2 and 4 at all concentrations were not cytotoxic to cells (Table 25).

TABLE 25

Zone index and lysis index for indirect cytotoxicity test of EDTA compounds 1-4. Zone index measures the clear zone in which cells do not stain with neutral red. The lysis index measures the number of cells affected within the zone of toxicity. All samples were tested in triplicate.

| Sample | Zone Index | Interpretation | Lysis Index | Interpretation |
| --- | --- | --- | --- | --- |
| DMEM | 0 | Non cytotoxic | 0 | Non cytotoxic |
| Water | 0 | Non cytotoxic | 0 | Non cytotoxic |
| Phenol | 5 | Cytotoxic | 3 | Cytotoxic |
| EDTA 2% | 3 | Cytotoxic | 2 | Non cytotoxic |
| EDTA 4% | 3 | Cytotoxic | 1 | Non cytotoxic |
| EDTA8% | 3 | Cytotoxic | 2 | Non cytotoxic |
| EDTA 10% | 3 | Cytotoxic | 3 | Cytotoxic |
| EDTA 15% | 3 | Cytotoxic | 3 | Cytotoxic |
| Compound 1 100 ppm | 3 | Cytotoxic | 1 | Non cytotoxic |
| Compound 1 50 ppm | 3 | Cytotoxic | 1 | Non cytotoxic |
| Compound 1 25 ppm | 2 | Non cytotoxic | 1 | Non cytotoxic |
| Compound 3 100 ppm | 3 | Cytotoxic | 1 | Non cytotoxic |
| Compound 3 50 ppm | 2 | Non cytotoxic | 1 | Non cytotoxic |
| Compound 3 25 ppm | 2 | Non cytotoxic | 1 | Non cytotoxic |
| Compound 2 100 ppm | 2 | Non cytotoxic | 1 | Non cytotoxic |
| Compound 2 50 ppm | 2 | Non cytotoxic | 1 | Non cytotoxic |
| Compound 2 25 ppm | 2 | Non cytotoxic | 1 | Non cytotoxic |
| Compound 4 100 ppm | 2 | Non cytotoxic | 1 | Non cytotoxic |
| Compound 4 50 ppm | 2 | Non cytotoxic | 1 | Non cytotoxic |
| Compound 4 25 ppm | 2 | Non cytotoxic | 1 | Non cytotoxic |

Table 25 demonstrates that the complexes were significantly lower in toxicity when compared to tetra sodium EDTA alone.

The efficacy of the EDTA-Ag$_2$—Zn compound (compound 4) in a wound biofilm model. At day 6, the untreated *S. aureus* wound biofilm was present in more than 50% of the tissue. After treatment with 100 ppm of the Ag—Zn$_2$-EDTA (compound 4), there appeared to be a reduced amount of microorganisms within the tissues, however there was no identifiable epidermis and the nuclei of fibroblasts in the dermal layer were faint.

Figure 4:
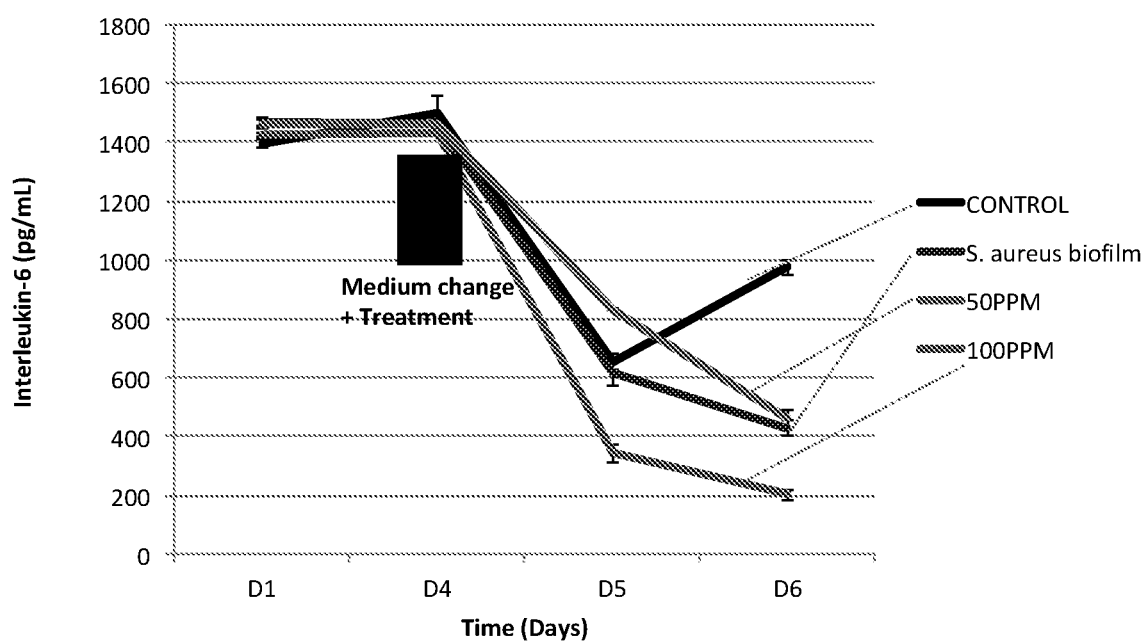
FIG. 4 shows IL-6 cytokine secretion from wounded, biofilm-containing Labskin following treatment with liquid Ag—$Zn_2$-EDTA (compound 4).

Enzyme-linked immunosorbent assay (ELISA) was used to assess the secreted levels of the inflammatory cytokine interleukin-6 (IL-6) according to previously published methods (Foster, A. M., Baliwag, J., Chen, C. S., Guzman, A. M., Stoll, S. W., Gudjonsson, J. E., Ward, N. L. & Johnston, A. 2014, IL-36 promotes myeloid cell infiltration, activation, and inflammatory activity in skin, *The Journal of Immunology*, 192, 6053-6061). ELISA detection of secreted IL-6 in the same experiment showed a reduction in IL-6 in the *S. aureus* wound biofilm control (FIG. 4). Treatment of wound biofilm with the Ag—Zn$_2$-EDTA (compound 4), was shown to reduce the presence of microorganisms upon histological examination. The IL-6 levels were reduced further when compared to the *S. aureus* wound biofilm control.

FIG. 4 shows IL-6 cytokine secretion from wounded, biofilm-containing Labskin following treatment with liquid Ag—Zn$_2$-EDTA (compound 4). ELISA was used to assess the levels of IL-6 in conditioned cell culture medium.

Culture medium was changed at day 4, which accounts for the reduction in IL-6. Biofilms were treated with either 50 ppm or 100 ppm of EDTA compound 4. Tests were performed in duplicate. Error bars indicate standard deviation.

FIG. 4 demonstrates that the Ag—$Zn_2$-EDTA (compound 4) at 100 ppm caused a significant reduction in the inflammatory marker.

In summary, the present invention provides a metal-EDTA compound/complex for combatting biofilms and/or treating wounds. The compound/complex comprises EDTA and from two to four metal ions. Of those two to four metal ions, at least two are different metal ions selected from Ag, Al, Au, Ba, Bi, Tl, Ce, Co, Cu, Fe, Ga, Ir, Mo, Rh, Ru, Ti, and Zn ions. The metal-EDTA compound/complex may exhibit any one or more of anti-microbial, anti-biofilm and anti-inflammatory activities in use and may increase the susceptibility of a biofilm and the microorganisms within said biofilm to attack by anti-microbial agents, helping to remove and sanitise the biofilm. A composition, wound dressing and medical device comprising the metal-EDTA complex are also provided. Uses of the metal-EDTA compound/complex as a medicament and/or to sanitise and/or substantially remove a biofilm from a substrate are also disclosed.

Although a few preferred embodiments have been shown and described, it will be appreciated by those skilled in the art that various changes and modifications might be made without departing from the scope of the invention, as defined in the appended claims.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, and drawings), and/or all of the steps of any method or process so disclosed, may be combined in any combination, except combinations where at least some of such features and/or steps are mutually exclusive.

Each feature disclosed in this specification (including any accompanying claims, and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, and drawings), or to any novel one, or any novel combination, of the steps of any method or process so disclosed.

The invention claimed is:

1. A compound of formula $M_n$(EDTA); wherein:
   n is an integer from 2 to 4;
   each M is a metal ion; and
   $M_n$ comprises at least two different metal ions selected from Ag, Al, Au, Ba, Bi, Tl, Ce, Co, Cu, Fe, Ga, Ir, Mo, Rh, Ru, Ti, and Zn ions.

2. The compound according to claim 1, wherein n=3 or 4 and $M_n$ comprises two Ag ions.

3. The compound according to claim 1, wherein $M_n$ comprises at least one Ag ion and one Zn ion.

4. The compound according to claim 3, having the formula $Ag_2Zn$(EDTA).

5. The compound according to claim 1, wherein $M_n$ comprises at least one Ag ion and one Cu ion.

6. The compound according to claim 5, having the formula $Ag_2Cu$(EDTA).

7. A composition comprising one or more compounds according to claim 1.

8. The composition according to claim 7 which is a hydrogel which comprises the one or more compounds.

9. The composition according to claim 7, comprising fibres which are in contact with the one or more compounds.

10. The composition according to claim 7, wherein the composition comprises a non-metal ion anti-microbial agent.

11. The composition according to claim 7, wherein the composition comprises a surfactant.

12. A wound dressing comprising a compound according to claim 1.

13. A medical device comprising a compound according to claim 1.

14. A medicament comprising a compound according to claim 1.

15. A kit comprising a compound according to claim 1 and a medical device or wound dressing.

16. A wound dressing comprising a composition according to claim 7.

17. A medical device comprising a composition according to claim 7.

18. A medicament comprising a composition according to claim 7.

19. A kit comprising a composition according to claim 7 and a medical device or a wound dressing.

* * * * *